(12) United States Patent
Hovorka et al.

(10) Patent No.: US 8,858,635 B2
(45) Date of Patent: Oct. 14, 2014

(54) INTERVERTEBRAL DISC PROSTHESIS

(75) Inventors: Istvan Hovorka, Nice (FR); Pierre Bernard, Bordeaux (FR)

(73) Assignee: LDR Medical, Rosieres Pres Troyes (FR)

( * ) Notice: Subject to any disclaimer, the term of this patent is extended or adjusted under 35 U.S.C. 154(b) by 1276 days.

(21) Appl. No.: 11/051,710

(22) Filed: Feb. 4, 2005

(65) Prior Publication Data
US 2005/0197706 A1    Sep. 8, 2005

(30) Foreign Application Priority Data

Feb. 4, 2004    (FR) .................................... 04 010 24

(51) Int. Cl.
*A61F 2/44* (2006.01)
*A61F 2/30* (2006.01)
*A61F 2/46* (2006.01)
*A61F 2/00* (2006.01)
*A61B 17/34* (2006.01)

(52) U.S. Cl.
CPC ..... *A61F 2/4425* (2013.01); *A61F 2002/30571* (2013.01); *A61F 2002/4627* (2013.01); *A61F 2002/30331* (2013.01); *A61F 2002/30841* (2013.01); *A61F 2002/30365* (2013.01); *A61F 2002/30795* (2013.01); *A61F 2/0095* (2013.01); *A61F 2220/0033* (2013.01); *A61F 2002/30476* (2013.01); *A61F 2002/30662* (2013.01); *A61F 2002/30904* (2013.01); *A61F 2002/4622* (2013.01); *A61B 17/3468* (2013.01); *A61F 2002/30649* (2013.01); *A61F 2002/30673* (2013.01); *A61F 2/4611* (2013.01); *A61F 2220/0025* (2013.01); *A61F 2002/443* (2013.01); *A61F 2/30767* (2013.01); *A61F 2002/30387* (2013.01); *A61B 17/3472* (2013.01); *A61F 2002/30616* (2013.01); *A61F 2002/30685* (2013.01); *A61F 2002/30937* (2013.01); *A61F 2002/30369* (2013.01); *A61F 2002/30367* (2013.01)
USPC ..................................... 623/17.15; 623/17.11

(58) Field of Classification Search
CPC ................ A61F 2/44; A61F 2002/443; A61F 2002/448; A61F 2/4455
USPC .................. 623/17.11, 17.14–17.16; 62/17.14
See application file for complete search history.

(56) References Cited

U.S. PATENT DOCUMENTS 566,360 A    8/1896   White
1,436,573 A  11/1922  Choppinet et al.

(Continued)

FOREIGN PATENT DOCUMENTS

CA    2472708    2/2005
CA    2533473    3/2011

(Continued)

OTHER PUBLICATIONS

A biological basis for instantaneous centres of rotation of the vertebral column, N. Bouduk, B. Amevo, M. Pearcy, Proc Insititution Mechanical Engineers, Jun. 16, 1995, pp. 177-183.

(Continued)

*Primary Examiner* — Thomas J Sweet
*Assistant Examiner* — Christopher D Prone
(74) *Attorney, Agent, or Firm* — Denko Coburn Lauff LLP

(57) ABSTRACT

The disclosure relates to intervertebral disc prostheses, which may comprise at least three pieces including an upper plate, a lower plate, and a core mobile at least relative to the lower plate, the upper surface of the core being in contact with at least a part of the lower surface of the upper plate. Various embodiments have limit stops allowing friction to be limited, while limiting or preventing the movements of the core relative to the lower plate, in translation and in rotation, respectively, along an axis substantially parallel to the lower plate and about an axis substantially perpendicular to the lower plate, and have at least one hole disposed along the lower surface of the core facilitating sliding of the core relative to the upper surface of the lower plate with which it is in contact. Instruments for inserting intervertebral prostheses are also disclosed.

50 Claims, 7 Drawing Sheets

(56) References Cited

U.S. PATENT DOCUMENTS

| | | | |
|---|---|---|---|
| 2,836,442 A | 5/1958 | Moskovitz |
| 3,325,197 A | 6/1967 | Wehner |
| 3,374,786 A | 3/1968 | Callender et al. |
| 3,486,505 A | 12/1969 | Morrison |
| 3,791,380 A | 2/1974 | Dawidowski |
| 3,857,642 A | 12/1974 | Miller |
| 3,892,232 A | 7/1975 | Neufeld |
| 3,958,278 A | 5/1976 | Lee et al. |
| 4,009,712 A | 3/1977 | Burstein et al. |
| 4,074,542 A | 2/1978 | Hankosky et al. |
| 4,085,466 A | 4/1978 | Goodfellow et al. |
| 4,135,506 A | 1/1979 | Ulrich |
| 4,175,555 A | 11/1979 | Herbert |
| 4,185,762 A | 1/1980 | Froehlich |
| 4,237,875 A | 12/1980 | Termanini |
| 4,309,777 A | 1/1982 | Patil |
| 4,349,921 A | 9/1982 | Kuntz |
| 4,379,451 A | 4/1983 | Getscher |
| 4,409,974 A | 10/1983 | Freedland |
| 4,432,358 A | 2/1984 | Fixel |
| 4,488,543 A | 12/1984 | Tornier |
| 4,494,535 A | 1/1985 | Haig |
| 4,519,100 A | 5/1985 | Wills et al. |
| 4,561,432 A | 12/1985 | Mazor |
| 4,612,920 A | 9/1986 | Lower |
| 4,621,629 A | 11/1986 | Koeneman |
| 4,632,101 A | 12/1986 | Freedland |
| 4,653,489 A | 3/1987 | Tronzo |
| 4,655,778 A | 4/1987 | Koeneman |
| 4,657,001 A | 4/1987 | Fixel |
| 4,664,305 A | 5/1987 | Blake, III et al. |
| 4,714,469 A | 12/1987 | Kenna |
| 4,721,103 A | 1/1988 | Freedland |
| 4,756,711 A | 7/1988 | Mai et al. |
| 4,759,352 A | 7/1988 | Lozier |
| 4,759,766 A * | 7/1988 | Buettner-Janz et al. ... 623/17.15 |
| 4,759,769 A | 7/1988 | Hedman et al. |
| 4,787,378 A | 11/1988 | Sodhi |
| 4,787,908 A | 11/1988 | Wyss et al. |
| 4,790,303 A | 12/1988 | Steffee |
| 4,791,918 A | 12/1988 | Von Hasselbach |
| 4,863,476 A | 9/1989 | Shepperd |
| 4,874,389 A | 10/1989 | Downey |
| 4,892,545 A | 1/1990 | Day et al. |
| 4,898,156 A | 2/1990 | Gatturna et al. |
| 4,911,718 A | 3/1990 | Lee et al. |
| 4,932,975 A | 6/1990 | Main |
| 4,946,378 A | 8/1990 | Hirayama et al. |
| 4,946,468 A | 8/1990 | Li |
| 4,955,908 A | 9/1990 | Frey et al. |
| 4,955,916 A | 9/1990 | Carignan et al. |
| 4,964,403 A | 10/1990 | Karas et al. |
| 4,968,315 A | 11/1990 | Gatturna |
| 4,969,887 A | 11/1990 | Sodhi |
| 4,973,332 A | 11/1990 | Kummer |
| 4,973,333 A | 11/1990 | Treharne |
| 4,997,432 A | 3/1991 | Keller |
| 5,002,550 A | 3/1991 | Li |
| 5,002,576 A | 3/1991 | Fuhrmann et al. |
| 5,007,910 A | 4/1991 | Anapliotis et al. |
| 5,032,125 A | 7/1991 | Durham et al. |
| 5,041,114 A | 8/1991 | Chapman et al. |
| 5,041,116 A | 8/1991 | Wilson |
| 5,041,139 A | 8/1991 | Branemark |
| 5,046,513 A | 9/1991 | Gatturna et al. |
| 5,057,103 A | 10/1991 | Davis |
| 5,062,851 A | 11/1991 | Branemark |
| 5,071,437 A * | 12/1991 | Steffee ...................... 623/17.16 |
| 5,087,266 A | 2/1992 | Connell et al. |
| 5,098,433 A | 3/1992 | Freedland |
| 5,116,336 A | 5/1992 | Frigg |
| 5,122,130 A | 6/1992 | Keller |
| 5,123,926 A | 6/1992 | Pisharodi |
| 5,129,901 A | 7/1992 | Decoste |
| 5,171,281 A | 12/1992 | Parsons et al. |
| 5,176,681 A | 1/1993 | Lawes et al. |
| 5,192,303 A | 3/1993 | Gatturna et al. |
| 5,192,327 A | 3/1993 | Brantigan |
| 5,197,986 A | 3/1993 | Mikhail |
| 5,207,679 A | 5/1993 | Li |
| 5,217,486 A | 6/1993 | Rice et al. |
| 5,234,447 A | 8/1993 | Kaster et al. |
| 5,242,448 A | 9/1993 | Pettine et al. |
| 5,246,458 A | 9/1993 | Graham |
| 5,258,009 A | 11/1993 | Conners |
| 5,258,031 A | 11/1993 | Salib et al. |
| 5,290,312 A | 3/1994 | Kojimoto et al. |
| 5,300,074 A | 4/1994 | Frigg |
| 5,306,309 A | 4/1994 | Wagner et al. |
| 5,314,477 A * | 5/1994 | Marnay ...................... 623/17.15 |
| 5,324,292 A | 6/1994 | Meyers |
| 5,342,394 A | 8/1994 | Matsuno et al. |
| 5,356,410 A | 10/1994 | Pennig |
| 5,356,413 A | 10/1994 | Martins et al. |
| 5,358,526 A | 10/1994 | Tornier |
| 5,370,697 A | 12/1994 | Baumgartner |
| 5,372,599 A | 12/1994 | Martins |
| 5,397,364 A | 3/1995 | Kozak et al. |
| 5,401,269 A | 3/1995 | Buettner-Janz et al. |
| 5,417,692 A | 5/1995 | Goble et al. |
| 5,417,712 A | 5/1995 | Whittaker et al. |
| 5,425,773 A | 6/1995 | Boyd et al. |
| 5,429,641 A | 7/1995 | Gotfried |
| 5,437,674 A | 8/1995 | Worcel et al. |
| 5,443,514 A | 8/1995 | Steffee |
| 5,456,721 A | 10/1995 | Legrand |
| 5,458,601 A | 10/1995 | Young, Jr. et al. |
| 5,472,452 A | 12/1995 | Trott |
| 5,478,342 A | 12/1995 | Kohrs |
| 5,489,210 A | 2/1996 | Hanosh |
| 5,507,754 A | 4/1996 | Green et al. |
| 5,507,816 A | 4/1996 | Bullivant |
| 5,522,845 A | 6/1996 | Wenstrom, Jr. |
| 5,522,899 A | 6/1996 | Michelson |
| 5,531,792 A | 7/1996 | Huene |
| 5,534,004 A | 7/1996 | Santangelo |
| 5,534,029 A | 7/1996 | Shima |
| 5,534,030 A | 7/1996 | Navarro et al. |
| 5,545,229 A | 8/1996 | Parsons et al. |
| 5,549,617 A | 8/1996 | Green et al. |
| 5,554,191 A | 9/1996 | Lahille et al. |
| 5,556,431 A | 9/1996 | Buettner-Janz et al. |
| 5,562,689 A | 10/1996 | Green et al. |
| 5,562,738 A | 10/1996 | Boyd et al. |
| 5,571,104 A | 11/1996 | Li |
| 5,571,109 A | 11/1996 | Bertagnoli |
| 5,571,189 A | 11/1996 | Kuslich |
| 5,578,035 A | 11/1996 | Lin |
| 5,591,168 A | 1/1997 | Judet et al. |
| 5,593,409 A | 1/1997 | Michelson |
| 5,609,635 A | 3/1997 | Michelson |
| 5,609,636 A | 3/1997 | Kohrs et al. |
| 5,613,974 A | 3/1997 | Andreas et al. |
| 5,620,012 A | 4/1997 | Benderev et al. |
| 5,643,321 A | 7/1997 | McDevitt |
| 5,645,596 A | 7/1997 | Kim |
| 5,655,698 A | 8/1997 | Yoon et al. |
| 5,674,294 A | 10/1997 | Bainville et al. |
| 5,676,701 A | 10/1997 | Yuan et al. |
| 5,676,702 A | 10/1997 | Ratron |
| 5,683,464 A | 11/1997 | Wagner et al. |
| 5,683,465 A | 11/1997 | Shinn et al. |
| 5,702,449 A | 12/1997 | McKay |
| 5,702,450 A | 12/1997 | Bisserie |
| 5,702,472 A | 12/1997 | Huebner |
| 5,722,977 A | 3/1998 | Wilhelmy |
| 5,741,253 A | 4/1998 | Michelson |
| 5,766,252 A | 6/1998 | Henry et al. |
| 5,766,253 A | 6/1998 | Brosnahan, III |
| 5,772,661 A | 6/1998 | Michelson |
| 5,776,199 A | 7/1998 | Michelson |
| 5,782,832 A | 7/1998 | Larsen et al. |
| 5,782,919 A | 7/1998 | Zdeblick et al. |
| 5,797,909 A | 8/1998 | Michelson |

(56) References Cited

U.S. PATENT DOCUMENTS

| | | |
|---|---|---|
| 5,800,547 A | 9/1998 | Schafer et al. |
| 5,800,550 A | 9/1998 | Sertich |
| 5,807,403 A | 9/1998 | Beyar et al. |
| 5,824,094 A | 10/1998 | Serhan et al. |
| 5,827,328 A | 10/1998 | Buttermann |
| 5,865,848 A | 2/1999 | Baker |
| 5,888,224 A | 3/1999 | Beckers et al. |
| 5,888,226 A | 3/1999 | Rogozinski |
| 5,893,889 A | 4/1999 | Harrington |
| 5,895,427 A | 4/1999 | Kuslich et al. |
| 5,895,428 A | 4/1999 | Berry |
| 5,899,941 A | 5/1999 | Nishijima |
| 5,968,098 A | 10/1999 | Winslow |
| 5,980,522 A | 11/1999 | Koros et al. |
| 5,984,967 A | 11/1999 | Zdeblick et al. |
| 6,001,130 A | 12/1999 | Bryan et al. |
| 6,010,502 A | 1/2000 | Bagby |
| 6,033,438 A | 3/2000 | Bianchi et al. |
| 6,039,763 A | 3/2000 | Shelokov |
| 6,045,552 A | 4/2000 | Zucherman et al. |
| 6,063,088 A | 5/2000 | Winslow |
| 6,063,121 A | 5/2000 | Xavier et al. |
| 6,066,175 A | 5/2000 | Henderson et al. |
| 6,080,158 A | 6/2000 | Lin |
| 6,093,205 A | 7/2000 | McLeod et al. |
| 6,096,038 A | 8/2000 | Michelson |
| 6,096,080 A | 8/2000 | Nicholson et al. |
| 6,099,531 A | 8/2000 | Bonutti |
| 6,102,950 A | 8/2000 | Vaccaro |
| 6,113,637 A | 9/2000 | Gill et al. |
| 6,113,638 A | 9/2000 | Williams et al. |
| 6,129,763 A | 10/2000 | Chauvin et al. |
| 6,136,031 A | 10/2000 | Middleton |
| 6,146,421 A | 11/2000 | Gordon et al. |
| 6,146,422 A | 11/2000 | Lawson |
| 6,149,650 A | 11/2000 | Michelson |
| 6,156,067 A | 12/2000 | Bryan et al. |
| 6,179,873 B1 | 1/2001 | Zientek |
| 6,179,874 B1 | 1/2001 | Cauthen |
| 6,193,757 B1 | 2/2001 | Foley et al. |
| 6,206,922 B1 | 3/2001 | Zdeblick et al. |
| 6,210,412 B1 | 4/2001 | Michelson |
| 6,214,050 B1 | 4/2001 | Huene |
| 6,221,077 B1 | 4/2001 | Rinner et al. |
| 6,224,595 B1 | 5/2001 | Michelson |
| 6,224,607 B1 | 5/2001 | Michelson |
| 6,228,118 B1 | 5/2001 | Gordon |
| 6,231,609 B1 | 5/2001 | Mehdizadeh |
| 6,241,769 B1 | 6/2001 | Nicholson et al. |
| 6,245,072 B1 | 6/2001 | Zdeblick et al. |
| 6,258,094 B1 | 7/2001 | Nicholson et al. |
| 6,261,293 B1 | 7/2001 | Nicholson et al. |
| 6,264,656 B1 | 7/2001 | Michelson |
| 6,267,763 B1 | 7/2001 | Castro |
| 6,270,498 B1 | 8/2001 | Michelson |
| 6,277,149 B1 | 8/2001 | Boyle et al. |
| 6,283,998 B1 | 9/2001 | Eaton |
| 6,287,308 B1 | 9/2001 | Betz et al. |
| 6,296,664 B1 | 10/2001 | Middleton |
| 6,302,914 B1 | 10/2001 | Michelson |
| 6,306,170 B2 | 10/2001 | Ray |
| 6,315,797 B1 | 11/2001 | Middleton |
| 6,319,257 B1 | 11/2001 | Carignan et al. |
| 6,342,074 B1 | 1/2002 | Simpson |
| 6,344,057 B1 | 2/2002 | Rabbe et al. |
| 6,364,880 B1 | 4/2002 | Michelson |
| 6,368,350 B1 * | 4/2002 | Erickson et al. ........... 623/17.14 |
| 6,371,987 B1 | 4/2002 | Weiland et al. |
| 6,371,988 B1 | 4/2002 | Pafford et al. |
| 6,375,655 B1 | 4/2002 | Zdeblick et al. |
| 6,387,130 B1 | 5/2002 | Stone et al. |
| 6,395,035 B2 | 5/2002 | Bresina et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,413,278 B1 | 7/2002 | Marchosky |
| 6,416,551 B1 | 7/2002 | Keller |
| 6,419,703 B1 | 7/2002 | Fallin et al. |
| 6,419,704 B1 | 7/2002 | Ferree |
| 6,419,706 B1 | 7/2002 | Graf |
| 6,423,063 B1 | 7/2002 | Bonutti |
| 6,423,095 B1 | 7/2002 | Van Hoeck et al. |
| 6,440,168 B1 | 8/2002 | Cauthen |
| 6,447,512 B1 | 9/2002 | Landry et al. |
| 6,447,544 B1 | 9/2002 | Michelson |
| 6,447,546 B1 | 9/2002 | Bramlet et al. |
| 6,447,547 B1 | 9/2002 | Michelson |
| 6,468,310 B1 | 10/2002 | Ralph et al. |
| 6,471,724 B2 | 10/2002 | Zdeblick et al. |
| 6,478,800 B1 | 11/2002 | Fraser et al. |
| 6,478,823 B1 | 11/2002 | Michelson |
| 6,482,234 B1 | 11/2002 | Weber et al. |
| 6,485,517 B1 | 11/2002 | Michelson |
| 6,500,205 B1 | 12/2002 | Michelson |
| 6,506,216 B1 | 1/2003 | McCue et al. |
| 6,514,260 B1 | 2/2003 | Zdeblick et al. |
| 6,517,580 B1 | 2/2003 | Ramadan et al. |
| 6,520,967 B1 | 2/2003 | Cauthen |
| 6,520,996 B1 | 2/2003 | Manasas et al. |
| 6,524,312 B2 | 2/2003 | Landry et al. |
| 6,527,804 B1 | 3/2003 | Gauchet et al. |
| 6,527,806 B2 | 3/2003 | Ralph et al. |
| 6,540,753 B2 | 4/2003 | Cohen |
| 6,540,785 B1 | 4/2003 | Gill et al. |
| 6,558,423 B1 | 5/2003 | Michelson |
| 6,558,424 B2 | 5/2003 | Thalgott |
| 6,565,605 B2 | 5/2003 | Goble et al. |
| 6,572,653 B1 | 6/2003 | Simonson |
| 6,579,291 B1 | 6/2003 | Keith et al. |
| 6,579,320 B1 | 6/2003 | Gauchet et al. |
| 6,582,468 B1 | 6/2003 | Gauchet et al. |
| 6,592,624 B1 | 7/2003 | Fraser et al. |
| 6,599,320 B1 | 7/2003 | Kuslich et al. |
| 6,607,530 B1 | 8/2003 | Carl et al. |
| 6,607,558 B2 | 8/2003 | Kuras |
| 6,610,089 B1 | 8/2003 | Liu et al. |
| 6,610,092 B2 | 8/2003 | Ralph et al. |
| 6,610,093 B1 | 8/2003 | Pisharodi |
| 6,613,091 B1 | 9/2003 | Zdeblick et al. |
| 6,616,671 B2 | 9/2003 | Landry et al. |
| 6,641,614 B1 | 11/2003 | Wagner et al. |
| 6,645,206 B1 | 11/2003 | Zdeblick et al. |
| 6,645,249 B2 | 11/2003 | Ralph et al. |
| 6,648,893 B2 | 11/2003 | Dudasik |
| 6,652,533 B2 | 11/2003 | O'Neil |
| 6,652,586 B2 | 11/2003 | Hunter et al. |
| 6,656,224 B2 | 12/2003 | Middleton |
| 6,669,730 B2 | 12/2003 | Ralph et al. |
| 6,669,731 B2 | 12/2003 | Ralph et al. |
| 6,669,732 B2 | 12/2003 | Serhan et al. |
| 6,673,113 B2 | 1/2004 | Ralph et al. |
| 6,679,887 B2 | 1/2004 | Nicholson et al. |
| 6,679,915 B1 | 1/2004 | Cauthen |
| 6,682,562 B2 | 1/2004 | Viart et al. |
| 6,695,851 B2 | 2/2004 | Zdeblick et al. |
| 6,695,882 B2 | 2/2004 | Bianchi et al. |
| 6,706,068 B2 | 3/2004 | Ferree |
| 6,709,439 B2 | 3/2004 | Rogers et al. |
| 6,709,458 B2 | 3/2004 | Michelson |
| 6,716,247 B2 | 4/2004 | Michelson |
| 6,719,794 B2 | 4/2004 | Gerber et al. |
| 6,723,127 B2 * | 4/2004 | Ralph et al. ................ 623/17.13 |
| 6,723,128 B2 | 4/2004 | Uk |
| 6,726,720 B2 | 4/2004 | Ross et al. |
| 6,730,088 B2 | 5/2004 | Yeh |
| 6,733,504 B2 | 5/2004 | Lin et al. |
| 6,733,532 B2 | 5/2004 | Gauchet et al. |
| 6,733,535 B2 | 5/2004 | Michelson |
| 6,736,850 B2 | 5/2004 | Davis |
| 6,740,117 B2 | 5/2004 | Ralph et al. |
| 6,740,118 B2 | 5/2004 | Eisermann et al. |
| 6,749,635 B1 | 6/2004 | Bryan |
| 6,749,636 B2 | 6/2004 | Michelson |
| 6,752,832 B2 | 6/2004 | Neumann |

(56) References Cited

U.S. PATENT DOCUMENTS

| | | |
|---|---|---|
| 6,755,841 B2 | 6/2004 | Fraser et al. |
| 6,764,512 B2 | 7/2004 | Keller |
| 6,764,515 B2 | 7/2004 | Ralph et al. |
| 6,767,367 B1 | 7/2004 | Michelson |
| 6,770,074 B2 | 8/2004 | Michelson |
| 6,770,095 B2 | 8/2004 | Grinberg et al. |
| 6,770,096 B2 | 8/2004 | Bolger et al. |
| 6,793,678 B2 | 9/2004 | Hawkins |
| 6,793,679 B2 | 9/2004 | Michelson |
| 6,800,093 B2 | 10/2004 | Nicholson et al. |
| 6,805,714 B2 | 10/2004 | Sutcliffe |
| 6,808,537 B2 | 10/2004 | Michelson |
| 6,814,737 B2 | 11/2004 | Cauthen |
| 6,824,565 B2 | 11/2004 | Muhanna et al. |
| 6,835,206 B2 | 12/2004 | Jackson |
| 6,849,093 B2 | 2/2005 | Michelson |
| 6,890,355 B2 | 5/2005 | Michelson |
| 6,899,735 B2 | 5/2005 | Coates et al. |
| 6,902,580 B2 | 6/2005 | Fallin et al. |
| 6,916,340 B2 | 7/2005 | Metzger et al. |
| 6,923,811 B1 | 8/2005 | Carl et al. |
| 6,923,830 B2 | 8/2005 | Michelson |
| 6,936,071 B1 | 8/2005 | Marnay et al. |
| 6,955,691 B2 | 10/2005 | Chae et al. |
| 6,962,606 B2 | 11/2005 | Michelson |
| 6,964,686 B2 | 11/2005 | Gordon |
| 6,966,929 B2 | 11/2005 | Mitchell |
| 6,972,019 B2 | 12/2005 | Michelson |
| 6,972,035 B2 | 12/2005 | Michelson |
| 6,981,975 B2 | 1/2006 | Michelson |
| 6,984,234 B2 | 1/2006 | Bray |
| 6,984,245 B2 | 1/2006 | McGahan et al. |
| 6,986,789 B2 | 1/2006 | Schultz et al. |
| 6,994,727 B2 | 2/2006 | Khandkar et al. |
| 7,001,385 B2 | 2/2006 | Bonutti |
| 7,001,432 B2 * | 2/2006 | Keller et al. ............... 623/17.14 |
| 7,008,453 B1 | 3/2006 | Michelson |
| 7,011,684 B2 | 3/2006 | Eckman |
| 7,025,787 B2 | 4/2006 | Bryan et al. |
| 7,033,394 B2 | 4/2006 | Michelson |
| 7,041,135 B2 | 5/2006 | Michelson |
| 7,041,136 B2 | 5/2006 | Goble et al. |
| 7,056,344 B2 | 6/2006 | Huppert et al. |
| 7,060,097 B2 | 6/2006 | Fraser et al. |
| 7,060,099 B2 | 6/2006 | Carli et al. |
| 7,063,701 B2 | 6/2006 | Michelson |
| 7,063,702 B2 | 6/2006 | Michelson |
| 7,066,961 B2 | 6/2006 | Michelson |
| 7,074,237 B2 | 7/2006 | Goble et al. |
| 7,090,698 B2 | 8/2006 | Goble et al. |
| 7,094,239 B1 | 8/2006 | Michelson |
| 7,105,023 B2 | 9/2006 | Eckman |
| 7,105,024 B2 | 9/2006 | Richelsoph |
| 7,112,206 B2 | 9/2006 | Michelson |
| 7,118,579 B2 | 10/2006 | Michelson |
| 7,118,580 B1 | 10/2006 | Byersdorff et al. |
| 7,118,598 B2 | 10/2006 | Michelson |
| 7,128,760 B2 | 10/2006 | Michelson |
| 7,128,761 B2 | 10/2006 | Kuras et al. |
| 7,147,665 B1 | 12/2006 | Bryan et al. |
| 7,153,325 B2 | 12/2006 | Kim et al. |
| 7,163,561 B2 | 1/2007 | Michelson |
| 7,169,153 B2 | 1/2007 | Keller |
| 7,175,662 B2 | 2/2007 | Link et al. |
| 7,179,294 B2 | 2/2007 | Eisermann et al. |
| 7,198,644 B2 | 4/2007 | Schultz et al. |
| 7,204,851 B2 | 4/2007 | Trieu et al. |
| 7,204,852 B2 | 4/2007 | Marnay et al. |
| 7,211,112 B2 | 5/2007 | Baynham et al. |
| 7,217,291 B2 | 5/2007 | Zucherman et al. |
| 7,217,292 B2 | 5/2007 | Ralph et al. |
| 7,217,293 B2 | 5/2007 | Branch, Jr. |
| 7,223,289 B2 | 5/2007 | Trieu et al. |
| 7,232,463 B2 | 6/2007 | Falahee |
| 7,232,464 B2 | 6/2007 | Mathieu et al. |
| 7,291,170 B2 | 11/2007 | Huppert |
| 7,326,248 B2 | 2/2008 | Michelson |
| 7,326,250 B2 | 2/2008 | Beaurain et al. |
| 7,410,501 B2 | 8/2008 | Michelson |
| 7,419,505 B2 | 9/2008 | Fleischmann et al. |
| 7,431,735 B2 | 10/2008 | Liu et al. |
| 7,435,262 B2 | 10/2008 | Michelson |
| 7,442,209 B2 | 10/2008 | Michelson |
| 7,445,635 B2 | 11/2008 | Fallin et al. |
| 7,445,636 B2 | 11/2008 | Michelson |
| 7,455,692 B2 | 11/2008 | Michelson |
| 7,465,317 B2 | 12/2008 | Malberg et al. |
| 7,481,840 B2 | 1/2009 | Zucherman et al. |
| 7,494,507 B2 | 2/2009 | Dixon et al. |
| 7,494,508 B2 | 2/2009 | Zeegers |
| 7,503,933 B2 | 3/2009 | Michelson |
| 7,517,363 B2 | 4/2009 | Rogers et al. |
| 7,540,882 B2 | 6/2009 | Michelson |
| 7,566,345 B1 | 7/2009 | Fallin et al. |
| 7,575,599 B2 | 8/2009 | de Villiers et al. |
| 7,575,600 B2 | 8/2009 | Zucherman et al. |
| 7,588,590 B2 | 9/2009 | Chervitz et al. |
| 7,591,851 B2 | 9/2009 | Winslow et al. |
| 7,594,931 B2 | 9/2009 | Louis et al. |
| 7,594,932 B2 | 9/2009 | Aferzon et al. |
| 7,601,170 B2 | 10/2009 | Winslow et al. |
| 7,608,107 B2 | 10/2009 | Michelson |
| 7,611,538 B2 | 11/2009 | Belliard et al. |
| 7,618,453 B2 | 11/2009 | Goble et al. |
| 7,618,455 B2 | 11/2009 | Goble et al. |
| 7,618,456 B2 | 11/2009 | Mathieu et al. |
| 7,621,955 B2 | 11/2009 | Goble et al. |
| 7,621,956 B2 | 11/2009 | Paul et al. |
| 7,621,958 B2 | 11/2009 | Zdeblick et al. |
| 7,632,282 B2 | 12/2009 | Dinville |
| 7,637,951 B2 | 12/2009 | Michelson |
| 7,637,954 B2 | 12/2009 | Michelson |
| 7,641,690 B2 | 1/2010 | Abdou |
| 7,655,027 B2 | 2/2010 | Michelson |
| 7,658,766 B2 | 2/2010 | Melkent et al. |
| 7,682,396 B2 | 3/2010 | Beaurain et al. |
| 7,695,516 B2 | 4/2010 | Zeegers |
| 7,695,517 B2 | 4/2010 | Benzel et al. |
| 7,708,776 B1 | 5/2010 | Blain et al. |
| 7,717,959 B2 | 5/2010 | William et al. |
| 7,727,280 B2 | 6/2010 | McLuen |
| 7,749,252 B2 | 7/2010 | Zucherman et al. |
| 7,749,274 B2 | 7/2010 | Razian |
| 7,753,937 B2 | 7/2010 | Chervitz et al. |
| 7,771,473 B2 | 8/2010 | Thramann |
| 7,771,475 B2 | 8/2010 | Michelson |
| 7,771,478 B2 | 8/2010 | Navarro et al. |
| 7,776,090 B2 | 8/2010 | Winslow et al. |
| 7,780,670 B2 | 8/2010 | Bonutti |
| 7,789,914 B2 | 9/2010 | Michelson |
| 7,794,502 B2 | 9/2010 | Michelson |
| 7,799,053 B2 | 9/2010 | Haid, Jr. et al. |
| 7,799,057 B2 | 9/2010 | Hudgins et al. |
| 7,799,081 B2 | 9/2010 | McKinley |
| 7,811,326 B2 | 10/2010 | Braddock, Jr. et al. |
| 7,819,903 B2 | 10/2010 | Fraser et al. |
| 7,824,445 B2 | 11/2010 | Biro et al. |
| 7,833,255 B2 | 11/2010 | Chow et al. |
| 7,842,088 B2 | 11/2010 | Rashbaum et al. |
| 7,846,207 B2 | 12/2010 | Lechmann et al. |
| 7,850,731 B2 | 12/2010 | Brittan et al. |
| 7,850,732 B2 | 12/2010 | Heinz |
| 7,850,733 B2 | 12/2010 | Baynham et al. |
| 7,862,616 B2 | 1/2011 | Lechmann et al. |
| 7,871,441 B2 | 1/2011 | Eckman |
| 7,875,076 B2 | 1/2011 | Mathieu et al. |
| 7,887,591 B2 | 2/2011 | Aebi et al. |
| 7,892,261 B2 | 2/2011 | Bonutti |
| 7,892,286 B2 | 2/2011 | Michelson |
| 7,896,919 B2 | 3/2011 | Belliard et al. |
| 7,909,871 B2 | 3/2011 | Abdou |
| 7,914,560 B2 | 3/2011 | Hoy et al. |
| 7,922,729 B2 | 4/2011 | Michelson |
| 7,931,674 B2 | 4/2011 | Zucherman et al. |

(56) References Cited

U.S. PATENT DOCUMENTS

| | | |
|---|---|---|
| 7,931,840 B2 | 4/2011 | Michelson |
| 7,935,149 B2 | 5/2011 | Michelson |
| 7,951,198 B2 | 5/2011 | Sucec et al. |
| 7,955,390 B2 | 6/2011 | Fallin et al. |
| 7,972,337 B2 | 7/2011 | Boyajian et al. |
| 7,972,363 B2 | 7/2011 | Moskowitz et al. |
| 7,972,365 B2 | 7/2011 | Michelson |
| 7,976,566 B2 | 7/2011 | Michelson |
| 7,985,255 B2 | 7/2011 | Bray et al. |
| 7,985,258 B2 | 7/2011 | Zdeblick et al. |
| 7,993,373 B2 | 8/2011 | Hoy et al. |
| 7,998,177 B2 | 8/2011 | Hoy et al. |
| 7,998,178 B2 | 8/2011 | Hoy et al. |
| 7,998,211 B2 | 8/2011 | Baccelli et al. |
| 8,002,835 B2 | 8/2011 | Zeegers |
| 8,007,534 B2 | 8/2011 | Michelson |
| 8,021,401 B2 | 9/2011 | Carl et al. |
| 8,021,430 B2 | 9/2011 | Michelson |
| 8,043,334 B2 | 10/2011 | Fisher et al. |
| 8,062,336 B2 | 11/2011 | Triplett et al. |
| 8,062,375 B2 | 11/2011 | Glerum et al. |
| 8,066,741 B2 | 11/2011 | Fallin et al. |
| 8,066,749 B2 | 11/2011 | Winslow et al. |
| 8,070,816 B2 | 12/2011 | Taylor |
| 8,070,819 B2 | 12/2011 | Aferzon et al. |
| 8,075,593 B2 | 12/2011 | Hess |
| 8,075,618 B2 | 12/2011 | Trieu et al. |
| 8,075,621 B2 | 12/2011 | Michelson |
| 8,114,082 B2 | 2/2012 | Boyajian et al. |
| 8,257,439 B2 | 9/2012 | Zeegers |
| 8,267,999 B2 | 9/2012 | Beaurain et al. |
| 8,343,219 B2 | 1/2013 | Allain et al. |
| 8,388,684 B2 | 3/2013 | Bao et al. |
| 8,439,931 B2 | 5/2013 | Dinville |
| 2001/0020185 A1 | 9/2001 | Ray |
| 2002/0035400 A1 | 3/2002 | Bryan et al. |
| 2002/0040243 A1 | 4/2002 | Attali et al. |
| 2002/0070565 A1 | 6/2002 | Szapucki et al. |
| 2002/0087212 A1 | 7/2002 | James et al. |
| 2002/0143343 A1 | 10/2002 | Castro |
| 2002/0161444 A1 | 10/2002 | Choi |
| 2002/0165613 A1 | 11/2002 | Lin et al. |
| 2002/0193880 A1 | 12/2002 | Fraser |
| 2003/0028249 A1 | 2/2003 | Baccelli et al. |
| 2003/0055503 A1 | 3/2003 | O'Neil |
| 2003/0069586 A1 | 4/2003 | Errico et al. |
| 2003/0074075 A1 | 4/2003 | Thomas, Jr. et al. |
| 2003/0093153 A1 | 5/2003 | Banick et al. |
| 2003/0093156 A1 | 5/2003 | Metzger et al. |
| 2003/0109928 A1 | 6/2003 | Pasquet et al. |
| 2003/0135279 A1 | 7/2003 | Michelson |
| 2003/0149438 A1 | 8/2003 | Nichols et al. |
| 2003/0171814 A1 | 9/2003 | Muhanna et al. |
| 2003/0187436 A1 | 10/2003 | Bolger et al. |
| 2003/0187506 A1 | 10/2003 | Ross et al. |
| 2003/0195514 A1 | 10/2003 | Trieu et al. |
| 2003/0220691 A1 | 11/2003 | Songer et al. |
| 2003/0233145 A1 | 12/2003 | Landry et al. |
| 2004/0002758 A1 | 1/2004 | Landry et al. |
| 2004/0002761 A1 | 1/2004 | Rogers et al. |
| 2004/0010312 A1 | 1/2004 | Enayati |
| 2004/0010316 A1 | 1/2004 | William et al. |
| 2004/0024406 A1 | 2/2004 | Ralph et al. |
| 2004/0030387 A1 | 2/2004 | Landry et al. |
| 2004/0034423 A1 | 2/2004 | Lyons et al. |
| 2004/0073309 A1 | 4/2004 | Bianchi et al. |
| 2004/0073311 A1 | 4/2004 | Ferree |
| 2004/0083000 A1 | 4/2004 | Keller et al. |
| 2004/0093082 A1 | 5/2004 | Ferree |
| 2004/0093083 A1 | 5/2004 | Branch et al. |
| 2004/0102846 A1 | 5/2004 | Keller et al. |
| 2004/0111160 A1 | 6/2004 | Evans et al. |
| 2004/0117022 A1 | 6/2004 | Marney et al. |
| 2004/0133278 A1 | 7/2004 | Marino et al. |
| 2004/0133281 A1 | 7/2004 | Khandkar et al. |
| 2004/0143332 A1 | 7/2004 | Krueger et al. |
| 2004/0148029 A1 | 7/2004 | Bianchi et al. |
| 2004/0153157 A1 | 8/2004 | Keller |
| 2004/0158254 A1 | 8/2004 | Eisermann |
| 2004/0158328 A1 | 8/2004 | Eisermann |
| 2004/0162617 A1 | 8/2004 | Zucherman et al. |
| 2004/0172020 A1 | 9/2004 | Beaurain et al. |
| 2004/0193273 A1 | 9/2004 | Huang |
| 2004/0199254 A1 | 10/2004 | Louis et al. |
| 2004/0210219 A1 | 10/2004 | Bray |
| 2004/0210313 A1 | 10/2004 | Michelson |
| 2004/0220582 A1 | 11/2004 | Keller |
| 2004/0225295 A1 | 11/2004 | Zubok et al. |
| 2004/0225363 A1 | 11/2004 | Richelsoph |
| 2004/0225364 A1 | 11/2004 | Richelsoph |
| 2004/0243238 A1 | 12/2004 | Arnin et al. |
| 2004/0243240 A1 | 12/2004 | Beaurain et al. |
| 2004/0254577 A1 | 12/2004 | Delecrin et al. |
| 2004/0254643 A1 | 12/2004 | Jackson |
| 2005/0010215 A1 | 1/2005 | Delecrin et al. |
| 2005/0015094 A1 | 1/2005 | Keller |
| 2005/0015095 A1 | 1/2005 | Keller |
| 2005/0015149 A1 | 1/2005 | Michelson |
| 2005/0021042 A1 | 1/2005 | Marnay et al. |
| 2005/0027359 A1 | 2/2005 | Mashburn |
| 2005/0027363 A1 | 2/2005 | Gordon |
| 2005/0033305 A1 | 2/2005 | Schultz |
| 2005/0033428 A1 | 2/2005 | Keller |
| 2005/0033435 A1 | 2/2005 | Belliard et al. |
| 2005/0033437 A1 | 2/2005 | Bao et al. |
| 2005/0033438 A1 | 2/2005 | Schultz |
| 2005/0038512 A1 | 2/2005 | Michelson |
| 2005/0038516 A1 | 2/2005 | Spoonamore |
| 2005/0043798 A1 | 2/2005 | Eckman |
| 2005/0043800 A1 | 2/2005 | Paul et al. |
| 2005/0043804 A1 | 2/2005 | Gordon et al. |
| 2005/0049590 A1 | 3/2005 | Alleyne et al. |
| 2005/0060034 A1 | 3/2005 | Berry et al. |
| 2005/0060037 A1 | 3/2005 | Michelson |
| 2005/0065608 A1 | 3/2005 | Michelson |
| 2005/0065611 A1 | 3/2005 | Huppert et al. |
| 2005/0071009 A1 | 3/2005 | Muhanna et al. |
| 2005/0085911 A1 | 4/2005 | Link |
| 2005/0085917 A1 | 4/2005 | Marney et al. |
| 2005/0107788 A1 | 5/2005 | Beaurain et al. |
| 2005/0113926 A1 | 5/2005 | Zucherman et al. |
| 2005/0119665 A1 | 6/2005 | Keller |
| 2005/0131542 A1 | 6/2005 | Benzel et al. |
| 2005/0131544 A1 | 6/2005 | Kuras et al. |
| 2005/0143733 A1 | 6/2005 | Petit |
| 2005/0143824 A1 | 6/2005 | Richelsoph et al. |
| 2005/0143825 A1 | 6/2005 | Enayati |
| 2005/0149189 A1 | 7/2005 | Mokhtar et al. |
| 2005/0154462 A1 | 7/2005 | Zucherman et al. |
| 2005/0159818 A1 | 7/2005 | Blain |
| 2005/0165408 A1 | 7/2005 | Puno et al. |
| 2005/0165485 A1 | 7/2005 | Trieu |
| 2005/0171610 A1 | 8/2005 | Humphreys et al. |
| 2005/0192671 A1 | 9/2005 | Bao et al. |
| 2005/0197705 A1 | 9/2005 | Arnin et al. |
| 2005/0197706 A1 | 9/2005 | Hovorka et al. |
| 2005/0216086 A1 | 9/2005 | Marik et al. |
| 2005/0216092 A1 | 9/2005 | Marik et al. |
| 2005/0228500 A1 | 10/2005 | Kim et al. |
| 2005/0234553 A1 | 10/2005 | Gordon |
| 2005/0240273 A1 | 10/2005 | Khandkar et al. |
| 2005/0246024 A1 | 11/2005 | Zeegers |
| 2005/0251260 A1 | 11/2005 | Gerber et al. |
| 2005/0256579 A1 | 11/2005 | Keller et al. |
| 2005/0267581 A1 | 12/2005 | Marnay et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283242 A1 | 12/2005 | Zucherman et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |

(56) References Cited

U.S. PATENT DOCUMENTS

| | | |
|---|---|---|
| 2005/0283248 A1 | 12/2005 | Gordon et al. |
| 2006/0015183 A1 | 1/2006 | Gilbert et al. |
| 2006/0016768 A1 | 1/2006 | Grichar et al. |
| 2006/0020341 A1 | 1/2006 | Schneid et al. |
| 2006/0030860 A1 | 2/2006 | Peterman |
| 2006/0036261 A1 | 2/2006 | McDonnell |
| 2006/0036325 A1 | 2/2006 | Paul et al. |
| 2006/0036326 A1 | 2/2006 | Baumgartner et al. |
| 2006/0041313 A1 | 2/2006 | Allard et al. |
| 2006/0041314 A1 | 2/2006 | Millard |
| 2006/0058878 A1 | 3/2006 | Michelson |
| 2006/0069437 A1 | 3/2006 | Weber |
| 2006/0069441 A1 | 3/2006 | Zucherman et al. |
| 2006/0085076 A1 | 4/2006 | Krishna et al. |
| 2006/0085077 A1 | 4/2006 | Cook et al. |
| 2006/0089717 A1 | 4/2006 | Krishna et al. |
| 2006/0095136 A1 | 5/2006 | McLuen |
| 2006/0111783 A1 | 5/2006 | Aflatoon et al. |
| 2006/0116768 A1 | 6/2006 | Krueger et al. |
| 2006/0116769 A1 | 6/2006 | Marnay et al. |
| 2006/0122703 A1 | 6/2006 | Aebi et al. |
| 2006/0129244 A1 | 6/2006 | Ensign |
| 2006/0136063 A1 | 6/2006 | Zeegers |
| 2006/0142863 A1 | 6/2006 | Fraser et al. |
| 2006/0149273 A1 | 7/2006 | Ross et al. |
| 2006/0149371 A1 | 7/2006 | Marik et al. |
| 2006/0149378 A1 | 7/2006 | Chase et al. |
| 2006/0155377 A1 | 7/2006 | Beaurain et al. |
| 2006/0155378 A1 | 7/2006 | Eckman |
| 2006/0173544 A1 | 8/2006 | Gau |
| 2006/0178745 A1 | 8/2006 | Bartish, Jr. et al. |
| 2006/0178746 A1 | 8/2006 | Bartish, Jr. et al. |
| 2006/0190082 A1 | 8/2006 | Keller et al. |
| 2006/0200241 A1 | 9/2006 | Rothman et al. |
| 2006/0200242 A1 | 9/2006 | Rothman et al. |
| 2006/0200243 A1 | 9/2006 | Rothman et al. |
| 2006/0206208 A1 | 9/2006 | Michelson |
| 2006/0212123 A1 | 9/2006 | Lechmann et al. |
| 2006/0235520 A1 | 10/2006 | Pannu |
| 2006/0235526 A1 | 10/2006 | Lemaire |
| 2006/0241764 A1 | 10/2006 | Michelson |
| 2006/0253201 A1 | 11/2006 | McLuen |
| 2006/0259143 A1 | 11/2006 | Navarro et al. |
| 2006/0259147 A1 | 11/2006 | Krishna et al. |
| 2006/0265072 A1 | 11/2006 | Richelsoph |
| 2006/0282074 A1 | 12/2006 | Renaud et al. |
| 2006/0287728 A1 | 12/2006 | Mokhtar et al. |
| 2007/0010886 A1 | 1/2007 | Banick et al. |
| 2007/0010887 A1 | 1/2007 | Williams et al. |
| 2007/0016217 A1 | 1/2007 | Dinville |
| 2007/0016297 A1 | 1/2007 | Johnson |
| 2007/0016299 A1 | 1/2007 | Eckman |
| 2007/0032871 A1 | 2/2007 | Michelson |
| 2007/0055378 A1 | 3/2007 | Ankney et al. |
| 2007/0073403 A1 | 3/2007 | Lombardo et al. |
| 2007/0073404 A1 | 3/2007 | Rashbaum et al. |
| 2007/0088362 A1 | 4/2007 | Bonutti et al. |
| 2007/0100454 A1 | 5/2007 | Burgess et al. |
| 2007/0100455 A1 | 5/2007 | Parsons |
| 2007/0100456 A1 | 5/2007 | Dooris et al. |
| 2007/0118223 A1 | 5/2007 | Allard et al. |
| 2007/0123985 A1 | 5/2007 | Errico et al. |
| 2007/0149974 A1 | 6/2007 | Mangione |
| 2007/0162130 A1 | 7/2007 | Rashbaum et al. |
| 2007/0162137 A1 | 7/2007 | Kloss et al. |
| 2007/0179623 A1 | 8/2007 | Trieu et al. |
| 2007/0250167 A1 | 10/2007 | Bray et al. |
| 2007/0250168 A1 | 10/2007 | Lechmann et al. |
| 2007/0260249 A1 | 11/2007 | Boyajian et al. |
| 2007/0270951 A1 | 11/2007 | Davis et al. |
| 2007/0270954 A1 | 11/2007 | Wu |
| 2007/0270961 A1 | 11/2007 | Ferguson |
| 2007/0270967 A1 | 11/2007 | Fallin et al. |
| 2007/0276498 A1 | 11/2007 | Aebi et al. |
| 2007/0288094 A1 | 12/2007 | Krishna et al. |
| 2007/0299524 A1 | 12/2007 | Rivin |
| 2008/0027547 A1 | 1/2008 | Yu et al. |
| 2008/0027550 A1 | 1/2008 | Link et al. |
| 2008/0033555 A1 | 2/2008 | Link et al. |
| 2008/0033562 A1 | 2/2008 | Krishna et al. |
| 2008/0161930 A1 | 7/2008 | Carls et al. |
| 2008/0195211 A1 | 8/2008 | Lin et al. |
| 2008/0200984 A1 | 8/2008 | Jodaitis et al. |
| 2008/0234686 A1 | 9/2008 | Beaurain et al. |
| 2008/0249569 A1 | 10/2008 | Waugh et al. |
| 2008/0249575 A1 | 10/2008 | Waugh et al. |
| 2008/0249625 A1 | 10/2008 | Waugh et al. |
| 2008/0262504 A1 | 10/2008 | Ralph et al. |
| 2008/0281425 A1 | 11/2008 | Thalgott et al. |
| 2008/0294260 A1 | 11/2008 | Gray |
| 2008/0300634 A1 | 12/2008 | Gray |
| 2008/0300685 A1 | 12/2008 | Carls et al. |
| 2008/0306596 A1 | 12/2008 | Jones et al. |
| 2009/0030461 A1 | 1/2009 | Hoy et al. |
| 2009/0030519 A1 | 1/2009 | Falahee |
| 2009/0030520 A1 | 1/2009 | Biedermann et al. |
| 2009/0076615 A1 | 3/2009 | Duggal et al. |
| 2009/0099601 A1 | 4/2009 | Aferzon et al. |
| 2009/0105830 A1 | 4/2009 | Jones et al. |
| 2009/0105831 A1 | 4/2009 | Jones et al. |
| 2009/0105832 A1 | 4/2009 | Allain et al. |
| 2009/0118771 A1 | 5/2009 | Gonzalez-Hernandez |
| 2009/0125071 A1 | 5/2009 | Skinlo et al. |
| 2009/0132054 A1 | 5/2009 | Zeegers |
| 2009/0157188 A1 | 6/2009 | Zeegers |
| 2009/0164020 A1 | 6/2009 | Janowski et al. |
| 2009/0182429 A1 | 7/2009 | Humphreys et al. |
| 2009/0182430 A1 | 7/2009 | Tyber et al. |
| 2009/0192613 A1 | 7/2009 | Wing et al. |
| 2009/0192615 A1 | 7/2009 | Tyber et al. |
| 2009/0204219 A1 | 8/2009 | Beaurain et al. |
| 2009/0210062 A1 | 8/2009 | Thalgott et al. |
| 2009/0216241 A1 | 8/2009 | Dinville |
| 2009/0222100 A1 | 9/2009 | Cipoletti et al. |
| 2009/0228108 A1 | 9/2009 | Keller |
| 2009/0234455 A1 | 9/2009 | Moskowitz et al. |
| 2009/0265007 A1 | 10/2009 | Colleran |
| 2010/0004664 A1 | 1/2010 | Boyajian et al. |
| 2010/0049259 A1 | 2/2010 | Lambrecht et al. |
| 2010/0057206 A1 | 3/2010 | Duffield et al. |
| 2010/0070037 A1 | 3/2010 | Parry et al. |
| 2010/0082109 A1 | 4/2010 | Greenhalgh et al. |
| 2010/0087925 A1 | 4/2010 | Kostuik et al. |
| 2010/0106249 A1 | 4/2010 | Tyber et al. |
| 2010/0114317 A1 | 5/2010 | Lambrecht et al. |
| 2010/0121455 A1 | 5/2010 | Lambrecht et al. |
| 2010/0145459 A1 | 6/2010 | McDonough et al. |
| 2010/0145460 A1 | 6/2010 | McDonough et al. |
| 2010/0145463 A1 | 6/2010 | Michelson |
| 2010/0152856 A1 | 6/2010 | Overes et al. |
| 2010/0160984 A1 | 6/2010 | Berry et al. |
| 2010/0161057 A1 | 6/2010 | Berry et al. |
| 2010/0179655 A1 | 7/2010 | Hansell et al. |
| 2010/0185289 A1 | 7/2010 | Kirwan et al. |
| 2010/0204796 A1 | 8/2010 | Bae et al. |
| 2010/0211108 A1 | 8/2010 | Lemole, Jr. |
| 2010/0211176 A1 | 8/2010 | Greenhalgh |
| 2010/0217393 A1 | 8/2010 | Theofilos |
| 2010/0234958 A1 | 9/2010 | Linares |
| 2010/0249935 A1 | 9/2010 | Slivka et al. |
| 2010/0249937 A1 | 9/2010 | Blain et al. |
| 2010/0280618 A1 | 11/2010 | Jodaitis et al. |
| 2010/0286777 A1 | 11/2010 | Errico et al. |
| 2010/0286787 A1 | 11/2010 | Villiers et al. |
| 2010/0305700 A1 | 12/2010 | Ben-Arye et al. |
| 2010/0305704 A1 | 12/2010 | Messerli et al. |
| 2010/0312344 A1 | 12/2010 | Reiley |
| 2010/0312345 A1 | 12/2010 | Duffield et al. |
| 2010/0312346 A1 | 12/2010 | Kueenzi et al. |
| 2011/0004310 A1 | 1/2011 | Michelson |
| 2011/0009966 A1 | 1/2011 | Michelson |
| 2011/0015745 A1 | 1/2011 | Bucci |
| 2011/0035007 A1 | 2/2011 | Patel et al. |
| 2011/0040382 A1 | 2/2011 | Muhanna |

(56) References Cited

U.S. PATENT DOCUMENTS

| | | | |
|---|---|---|---|
| 2011/0054616 A1 | 3/2011 | Kamran et al. |
| 2011/0077738 A1 | 3/2011 | Ciupik et al. |
| 2011/0077739 A1 | 3/2011 | Rashbaum et al. |
| 2011/0082553 A1 | 4/2011 | Abdou |
| 2011/0087327 A1 | 4/2011 | Lechmann et al. |
| 2011/0093077 A1 | 4/2011 | Aebi et al. |
| 2011/0098747 A1 | 4/2011 | Donner et al. |
| 2011/0118843 A1 | 5/2011 | Mathieu et al. |
| 2011/0125267 A1 | 5/2011 | Michelson |
| 2011/0137420 A1 | 6/2011 | Michelson |
| 2011/0144703 A1 | 6/2011 | Krause et al. |
| 2011/0160860 A1 | 6/2011 | Johnston et al. |
| 2011/0166655 A1 | 7/2011 | Michelson |
| 2011/0166656 A1 | 7/2011 | Thalgott et al. |
| 2011/0166657 A1 | 7/2011 | Thalgott et al. |
| 2011/0166658 A1 | 7/2011 | Garber et al. |
| 2011/0172774 A1 | 7/2011 | Varela |
| 2011/0196492 A1 | 8/2011 | Lambrecht et al. |
| 2011/0196493 A1 | 8/2011 | Pimenta |
| 2011/0196494 A1 | 8/2011 | Yedlicka et al. |
| 2011/0202136 A1 | 8/2011 | Brittan et al. |
| 2011/0208311 A1 | 8/2011 | Janowski |
| 2011/0208313 A1 | 8/2011 | Michelson |
| 2011/0230969 A1 | 9/2011 | Biedermann et al. |
| 2011/0230971 A1 | 9/2011 | Donner et al. |
| 2011/0264227 A1 | 10/2011 | Boyajian et al. |
| 2011/0295371 A1 | 12/2011 | Moskowitz et al. |
| 2011/0301713 A1 | 12/2011 | Theofilos |
| 2011/0301714 A1 | 12/2011 | Theofilos |
| 2011/0313528 A1 | 12/2011 | Laubert et al. |
| 2012/0053693 A1 | 3/2012 | Zeegers |
| 2013/0226300 A1 | 8/2013 | Chataigner et al. |

FOREIGN PATENT DOCUMENTS

| | | | |
|---|---|---|---|
| DE | 2263842 A | 7/1974 |
| DE | 2804936 | 8/1979 |
| DE | 3023353 A | 4/1981 |
| DE | 8912648 U | 11/1990 |
| DE | 4328690 | 3/1995 |
| DE | 29911422 | 8/1999 |
| DE | 20310432 U | 9/2003 |
| DE | 20310433 U | 9/2003 |
| DE | 20320454 | 10/2004 |
| DE | 10323363 | 12/2004 |
| DE | 102004027986 | 7/2005 |
| EP | 42271 | 12/1981 |
| EP | 176728 | 4/1986 |
| EP | 0298235 A | 1/1989 |
| EP | 0317972 A | 5/1989 |
| EP | 0333990 A | 9/1989 |
| EP | 0356112 | 2/1990 |
| EP | 0512529 A | 11/1992 |
| EP | 0560141 A | 9/1993 |
| EP | 0566810 A1 | 10/1993 |
| EP | 0637439 | 2/1995 |
| EP | 0697200 | 2/1996 |
| EP | 0566810 B1 | 5/1996 |
| EP | 0738504 | 10/1996 |
| EP | 0747025 A1 | 12/1996 |
| EP | 0852934 | 7/1998 |
| EP | 0903126 | 3/1999 |
| EP | 0951879 | 10/1999 |
| EP | 0955021 A | 11/1999 |
| EP | 0978258 | 2/2000 |
| EP | 1222903 | 7/2002 |
| EP | 1250898 A1 | 10/2002 |
| EP | 1287795 | 3/2003 |
| EP | 1344506 | 9/2003 |
| EP | 1344508 | 9/2003 |
| EP | 1504733 | 2/2005 |
| EP | 1374806 | 12/2005 |
| FR | 2124815 A | 9/1972 |
| FR | 2372622 | 6/1978 |
| FR | 2632516 A | 12/1989 |
| FR | 2659226 A | 9/1991 |
| FR | 2716619 | 9/1995 |
| FR | 2718635 A1 | 3/1996 |
| FR | 2723841 | 3/1996 |
| FR | 2724108 A | 3/1996 |
| FR | 2730159 A1 | 8/1996 |
| FR | 2737656 | 2/1997 |
| FR | 2787019 | 12/1998 |
| FR | 2787021 A | 6/2000 |
| FR | 2824261 | 11/2002 |
| FR | 2831796 | 5/2003 |
| FR | 2843293 | 2/2004 |
| FR | 2846550 | 5/2004 |
| FR | 2865629 | 8/2005 |
| FR | 2865630 A1 | 8/2005 |
| FR | 2869528 | 11/2005 |
| FR | 2879436 | 6/2006 |
| FR | 2880795 | 7/2006 |
| FR | 2887762 | 1/2007 |
| FR | 2891135 | 3/2007 |
| FR | 2893838 | 6/2007 |
| FR | 2916956 | 12/2008 |
| JP | 2261446 | 10/1990 |
| WO | WO9011740 | 10/1990 |
| WO | WO9011740 A | 10/1990 |
| WO | WO9107931 | 6/1991 |
| WO | WO9113598 A | 9/1991 |
| WO | WO9301771 A | 2/1993 |
| WO | WO9404100 | 3/1994 |
| WO | WO9515133 | 6/1995 |
| WO | WO9817209 | 4/1998 |
| WO | WO9909914 | 3/1999 |
| WO | WO9953871 | 10/1999 |
| WO | WO9956675 A | 11/1999 |
| WO | WO9956676 | 11/1999 |
| WO | WO9965412 | 12/1999 |
| WO | WO9966864 | 12/1999 |
| WO | WO0053127 A | 9/2000 |
| WO | WO0074606 A | 12/2000 |
| WO | WO0101893 A | 1/2001 |
| WO | WO0119295 A | 3/2001 |
| WO | WO0141680 | 6/2001 |
| WO | WO0143620 | 6/2001 |
| WO | WO0162191 | 8/2001 |
| WO | WO02013732 | 2/2002 |
| WO | WO02058599 | 8/2002 |
| WO | WO02071960 | 9/2002 |
| WO | WO02089701 A2 | 11/2002 |
| WO | WO03005939 | 1/2003 |
| WO | WO03015646 | 2/2003 |
| WO | WO03026522 | 4/2003 |
| WO | WO03039400 A2 | 5/2003 |
| WO | WO03045262 | 6/2003 |
| WO | WO03059212 A | 7/2003 |
| WO | WO03075803 | 9/2003 |
| WO | WO03075804 A | 9/2003 |
| WO | WO2004034935 | 4/2004 |
| WO | WO2004039291 | 5/2004 |
| WO | WO2004041129 A1 | 5/2004 |
| WO | WO2004041131 | 5/2004 |
| WO | WO2004071360 | 8/2004 |
| WO | WO2004089256 | 10/2004 |
| WO | WO2005007040 | 1/2005 |
| WO | WO 2005007044 | 1/2005 |
| WO | WO2005046534 | 5/2005 |
| WO | WO2005051243 | 6/2005 |
| WO | WO2005074839 | 8/2005 |
| WO | WO2005104996 | 11/2005 |
| WO | WO2005117728 | 12/2005 |
| WO | WO2006016384 | 2/2006 |
| WO | WO2006047587 | 5/2006 |
| WO | WO2006062960 | 6/2006 |
| WO | WO2006120505 | 11/2006 |
| WO | WO2006130460 | 12/2006 |
| WO | WO2006136760 | 12/2006 |
| WO | WO2007000654 | 1/2007 |
| WO | WO2007034310 | 3/2007 |
| WO | WO2007063398 | 6/2007 |

(56) References Cited

FOREIGN PATENT DOCUMENTS

| WO | WO2007078978 | 7/2007 |
|---|---|---|
| WO | WO2008099277 | 8/2008 |
| WO | WO2008149223 | 12/2008 |
| WO | WO2009033100 | 3/2009 |
| WO | WO2011080535 | 7/2011 |
| WO | WO 2013124453 | 8/2013 |

OTHER PUBLICATIONS

A Multicenter Retrospective Study of the Clinical Results of the LINK SB Charite Intervertebral Prosthesis, S. L. Griffith, PhD, A. P. Shelokov, MD, K. Buttner-Janz, MD, Jean-Phillipe LeMaire, MD and W. S. Zeegers, MD, Spine, vol. 19, No. 16, pp. 1842-1849, Mar. 21, 1994.

A New Technique for the Three-Dimensional Study of the Spine in Vitro and In Vivo by Using a Motion-Analysis System, X. Liu, G. Fabry, K. Labey, L. Van Den Berghe, R. Van Audekercke, G. Molenaers, P. Moens, Journal of Spinal Disorders, vol. 10, No. 4, pp. 329-338, Jan. 30, 1997.

Alternatives to Spinal Fusion, J. P. Kostuik, Spinal Fusion, vol. 29, No. 4, Oct. 1998, pp. 701-415.

Centrode Patterns and Segmental Instability in Degenerative Disc Disease, S.D. Gertzban, MD, FRCSC, J. Seligman, MD, R. Holtby, MD, K.H. Chan, MD, A. Kapasouri, BSc, M. Tile, MD, BSc, (MED), FRCS© , and B. Cruickshank, MD, FRCPath, Spine, vol. 10., No. 3, pp. 257-261, Jan. 21, 1984.

Clinical Biomechanics of the Spine, A. A. White III, M. M. Panjabi, pp. 128-130, 2nd Edition, J.B. Lippincott Co., 1990.

Computer Analysis of Spinal Segment Motion in Degenerative Disc Disease With and Without Axial Loading, J.V. Seligman, S.D. Gertzbein, M. Tile, A., Kapasouri, Spine, vol. 9., No. 6, pp. 566-573, Dec. 31, 1983.

FR 2 718 635 Preliminary Search Report, National Institute of Industrial Property (France), Jan. 16, 1995.

FR 2 730 159 Preliminary Search Report, National Institute of Industrial Property (France), Sep. 29, 1995.

FR 2 824 261 Preliminary Search Report, National Institute of Industrial Property (France), Feb. 25, 2002.

FR 2 831 796 Preliminary Search Report, National Institute of Industrial Property (France), Aug. 2, 2002.

FR 2 846 550 Prelininary Search Report, National Institute of Industrial Property (France), Jul. 10, 2003.

FR 2 865 629 Preliminary Search Report, National Institute of Industrial Property (France), Sep. 14, 2004.

FR 2 865 630 Preliminary Search Report, National Institute of Industrial Property (France), Jan. 12, 2005.

FR 2 869 528 Preliminary Search Report, National Institute of Industrial Property (France), Dec. 13, 2004.

Instantantaneous Axis of Rotation as a Function of the Three Columns of the Spine, T. R. Haher, MD, M. O'Brien, MD, W. T. Felmly, MD, D. Welin, MD, G. Perrier, MD., J. Choueka, MD, V. Devlin, MD, A. Vassiliou, ME, and G. Chow, MS, Spine, vol. 17, No. 6, pp. S149-S154, Jan. 9, 1992.

Instantantaneous Axis of Rotation of the Lumbar Intervertebral Joints, M. J. Pearcy, H. Bogduk, Spine, vol. 13, No. 9, pp. 1033-1041, Nov. 15, 1987.

Mobidisc (website) 1 page, www.ldrmedical.fr/mobidisc.htm, Sep. 19, 2004.

Motion Characteristics of the Normal Lumbar Spine in Young Adults: Instantaneous of Axis of Rotation and Vertebral Center Motion Analysis, T. Yoshioka, H. Tsuji, N. Hirano and S. Sainoh, Journal of Spinal Disorders, vol. 3, No. 2, pp. 103-113, 1990.

PCT/IB02/02998 International Search Report, EPO, Sep. 16, 2003.
PCT/IB02/04642 International Search Report, EPO, Jul. 2, 2003.
PCT/IB05/00280 International Search Report, EPO, Jun. 24, 2005.
PCT/IB05/01151 International Search Report, EPO, Sep. 12, 2005.
PCT/IB03/04872 International Search Report, EPO, Mar. 3, 2004.
PCT/IB02/02998 International Preliminary Examination Report, EPO, Dec. 22, 2003.
PCT/IB02/04642 International Preliminary Examination Report, EPO, Apr. 1, 2004.
PCT/IB03/04872 International Preliminary Examination Report, EPO, Mar. 1, 2005.

Relocation of the Bending Axis During Flexion-Extension of Lumbar Intervertebral Discs and its Implications for Prolapse, J.A. Klein and D.W.L. Hukins,Spine, vol. 8, No. 6, pp. 659-664, Nov. 18, 1982.

The Effect of the Three Columns of the Spine on the Instantaneous Axis of Rotation in Flexion and Extension, T. R. Haher, M. Bergman, M. O'Brien, W. T. Felmly, J. Choueka, D. Welin, G. Chow, A. Vassiliou, Spine, vol. 16, No. 8, pp. S312-S318, Apr. 16, 1991.

USPTO OA of Feb. 6, 2007 in U.S. Appl. No. 11/109,276.
USPTO OA of Oct. 16, 2007 in U.S. Appl. No. 11/109,276.
USPTO OA of Jul. 24, 2008 in U.S. Appl. No. 11/109,276.
USPTO OA of Feb. 13, 2009 in U.S. Appl. No. 11/109,276.
Applicant's Reply to USPTO OA of Feb. 6, 2007 in U.S. Appl. No. 11/109,276.
Applicant's Reply to USPTO OA of Oct. 16, 2007 in U.S. Appl. No. 11/109,276.
Applicant's Reply to USPTO OA of Jul. 24, 2008 in U.S. Appl. No. 11/109,276.
Applicant's Response to USPTO OA of Feb. 13, 2009 in U.S. Appl. No. 11/109,276.
USPTO OA of Apr. 18, 2007 in U.S. Appl. No. 10/533,846.
Applicants' Response to USPTO OA of Apr. 18, 2007 in U.S. Appl. No. 10/533,846.
USPTO OA of Dec. 26, 2007 in U.S. Appl. No. 10/533,846.
Applicants' Response to USPTO OA of Dec. 26, 2007 in U.S. Appl. No. 10/533,846.
USPTO OA of Oct. 15, 2008 in U.S. Appl. No. 10/533,846.
Applicants' Response to USPTO OA of Oct. 15, 2008 in U.S. Appl. No. 10/533,846.
USPTO OA of Jan. 22, 2008 in U.S. Appl. No. 11/180,868.
Applicant's Response to USPTO OA of Jan. 22, 2008 in U.S. Appl. No. 11/180,868.
USPTO OA of Nov. 5, 2008 in U.S. Appl. No. 11/180,868.
Response to USPTO OA of Nov. 5, 2008 in U.S. Appl. No. 11/180,868.
USPTO OA of Apr. 13, 2009 in U.S. Appl. No. 11/341,007.
USPTO OA of Mar. 20, 2009 in U.S. Appl. No. 11/676,237.
USPTO OA of Feb. 18, 2009 in U.S. Appl. No. 11/632,253.
Applicants' Response to USPTO OA of Feb. 18, 2009 in U.S. Appl. No. 11/632,253.

World Intellectual Property Organization; International Preliminary Report on Patentability for PCT Pub'n No. WO2005074839; Jan. 16, 2006; WIPO; Geneva, Switzerland; all pages.

World Intellectual Property Organization; Written Opinon of the International Searching Authority for PCT Pub'n No. WO2005074839; Jun. 24, 2005; WIPO; Geneva, Switzerland; all pages.

European Patent Office; Office Action for Pub'n No. EP1711133; Mar. 2, 2009; EPO; Munich, Germany; all pages.

LDR Medical, by its attorneys; Reply to Office Action for Pub'n No. EP1711133; Jul. 22, 2009; EPO; Munich, Germany; all pages.

European Patent Office; Notice of Intention to Grant a European Patent for Pub'n No. EP1711133; Oct. 22, 2010; EPO; Munich, Germany; all pages.

U.S. Patent & Trademark Office; Notice of Allowance in U.S. Appl. No. 10/476,565; Nov. 29, 2007; USPTO; Alexandria, Virgina; All Pages.

LDR Medical, by its attorneys; Amendment After Final in U.S. Appl. No. 10/476,565; Nov. 29, 2007; USPTO; Alexandria, Virgina; All Pages.

LDR Medical, by its attorneys; Reply to Office Action in U.S. Appl. No. 12/025,677; Nov. 6, 2007; USPTO; Alexandria, Virgina; All Pages.

U.S. Patent & Trademark Office; Office Action in U.S. Appl. No. 10/476,565; May 7, 2007; USPTO; Alexandria, Virgina; All Pages.

LDR Medical, by its attorneys; Reply to Office Action in U.S. Appl. No. 12/025,677; Jan. 18, 2007; USPTO; Alexandria, Virgina; All Pages.

U.S. Patent & Trademark Office; Office Action in U.S. Appl. No. 10/476,565; Jul. 18, 2006; USPTO; Alexandria, Virgina; All Pages.

(56) References Cited

OTHER PUBLICATIONS

U.S. Patent & Trademark Office; Reply to Office Action in U.S. Appl. No. 12/025,677; Feb. 19, 2014; USPTO; Alexandria, Virgina; All Pages.
LDR Medical, by its attorneys; Reply to Office Action in U.S. Appl. No. 12/025,677; Dec. 20, 2013; USPTO; Alexandria, Virgina; All Pages.
U.S. Patent & Trademark Office; Office Action in U.S. Appl. No. 12/025,677; Jun. 20, 2013; USPTO; Alexandria, Virgina; All Pages.
LDR Medical, by its attorneys; Reply to Office Action in U.S. Appl. No. 12/025,677; Dec. 29, 2012; USPTO; Alexandria, Virgina; All Pages.
U.S. Patent & Trademark Office; Office Action in U.S. Appl. No. 12/025,677; Jun. 29, 2012; USPTO; Alexandria, Virgina; All Pages.
LDR Medical, by its attorneys; Reply to Office Action in U.S. Appl. No. 12/025,677; Apr. 9, 2012; USPTO; Alexandria, Virgina; All Pages.
U.S. Patent & Trademark Office; Office Action in U.S. Appl. No. 12/025,677; Oct. 7, 2011; USPTO; Alexandria, Virgina; All Pages.
U.S. Patent & Trademark Office; Notice of Allowance in U.S. Appl. No. 10/494,418; Sep. 20, 2005; USPTO; Alexandria, Virgina; All Pages.
U.S. Patent & Trademark Office; Notice of Allowance in U.S. Appl. No. 10/533,846; Nov. 4, 2009; USPTO; Alexandria, Virgina; All Pages.
LDR Medical, by its attorneys; Reply to Office Action in U.S. Appl. No. 10/533,846; Apr. 15, 2009; USPTO; Alexandria, Virgina; All Pages.
U.S. Patent & Trademark Office; Office Action in U.S. Appl. No. 10/533,846; Oct. 15, 2008; USPTO; Alexandria, Virgina; All Pages.
LDR Medical, by its attorneys; Reply to Office Action in U.S. Appl. No. 10/533,846; Jun. 25, 2008; USPTO; Alexandria, Virgina; All Pages.
U.S. Patent & Trademark Office; Office Action in U.S. Appl. No. 10/533,846; Dec. 26, 2007; USPTO; Alexandria, Virgina; All Pages.
LDR Medical, by its attorneys; Reply to Office Action in U.S. Appl. No. 10/533,846; Oct. 16, 2007; USPTO; Alexandria, Virgina; All Pages.
U.S. Patent & Trademark Office; Office Action in U.S. Appl. No. 10/533,846; Apr. 18, 2007; USPTO; Alexandria, Virgina; All Pages.
U.S. Patent & Trademark Office; Notice of Allowance in U.S. Appl. No. 12/424,364; Aug. 2, 2012; USPTO; Alexandria, Virgina; All Pages.
U.S. Patent & Trademark Office; Notice of Allowance in U.S. Appl. No. 12/424,364; Jul. 24, 2012; USPTO; Alexandria, Virgina; All Pages.
LDR Medical, by its attorneys; Reply to Office Action in U.S. Appl. No. 12/424,364; Jul. 6, 2012; USPTO; Alexandria, Virgina; All Pages.
U.S. Patent & Trademark Office; Office Action in U.S. Appl. No. 12/424,364; May 23, 2012; USPTO; Alexandria, Virgina; All Pages.
LDR Medical, by its attorneys; Interview Summary and Terminal Disclaimer in U.S. Appl. No. 12/424,364; May 22, 2012; USPTO; Alexandria, Virgina; All Pages.
LDR Medical, by its attorneys; Reply to Office Action in U.S. Appl. No. 12/424,364; Feb. 27, 2012; USPTO; Alexandria, Virgina; All Pages.
U.S. Patent & Trademark Office; Office Action in U.S. Appl. No. 12/424,364; Jan. 26, 2012; USPTO; Alexandria, Virgina; All Pages.
LDR Medical by its attorney; Reply to Office Action in U.S. Appl. No. 12/424,364; Nov. 18, 2011; USPTO; Alexandria, Virgina; All Pages.
U.S. Patent & Trademark Office; Office Action in U.S. Appl. No. 12/424,364; May 18, 2011; USPTO; Alexandria, Virgina; All Pages.
U.S. Patent & Trademark Office; Notice of Allowance in U.S. Appl. No. 13/616,448; Feb. 7, 2014; USPTO; Alexandria, Virgina; All Pages.
U.S. Patent & Trademark Office; Office Action in U.S. Appl. No. 13/616,448; Aug. 22, 2013; USPTO; Alexandria, Virgina; All Pages.
LDR Medical, by its attorneys; Request for Continued Examination in U.S. Appl. No. 11/051,710; Jul. 11, 2013; USPTO; Alexandria, Virgina; All Pages.
U.S. Patent & Trademark Office; Notice of Allowance in U.S. Appl. No. 11/051,710; Apr. 11, 2013; USPTO; Alexandria, Virgina; All Pages.
LDR Medical, by its attorneys; Appeal Brief in U.S. Appl. No. 11/051,710; Jan. 15, 2013; USPTO; Alexandria, Virgina; All Pages.
U.S. Patent & Trademark Office; Office Action in U.S. Appl. No. 11/051,710; Dec. 15, 2011; USPTO; Alexandria, Virgina; All Pages.
LDR Medical, by its attorneys; Reply to Office Action in U.S. Appl. No. 11/051,710; Oct. 11, 2011; USPTO; Alexandria, Virgina; All Pages.
U.S. Patent & Trademark Office; Office Action in U.S. Appl. No. 11/051,710; Apr. 11, 2011; USPTO; Alexandria, Virgina; All Pages.
LDR Medical, by its attorneys; Reply to Office Action in U.S. Appl. No. 11/051,710; Jan. 20, 2011; USPTO; Alexandria, Virgina; All Pages.
U.S. Patent & Trademark Office; Office Action in U.S. Appl. No. 11/051,710; Jul. 20, 2010; USPTO; Alexandria, Virgina; All Pages.
LDR Medical, by its attorneys; Reply to Office Action in U.S. Appl. No. 11/051,710; Apr. 26, 2010; USPTO; Alexandria, Virgina; All Pages.
U.S. Patent & Trademark Office; Office Action in U.S. Appl. No. 11/051,710; Oct. 26, 2009; USPTO; Alexandria, Virgina; All Pages.
U.S. Patent & Trademark Office; Notice of Allowance in U.S. Appl. No. 11/098,266; Apr. 21, 2008; USPTO; Alexandria, Virgina; All Pages.
LDR Medical, by its attorneys; Reply to Office Action in U.S. Appl. No. 11/098,266; Feb. 6, 2008; USPTO; Alexandria, Virgina; All Pages.
U.S. Patent & Trademark Office; Office Action in U.S. Appl. No. 11/098,266; Aug. 6, 2007; USPTO; Alexandria, Virgina; All Pages.
LDR Medical, by its attorneys; Reply to Office Action in U.S. Appl. No. 11/098,266; May 23, 2007; USPTO; Alexandria, Virgina; All Pages.
U.S. Patent & Trademark Office; Office Action in U.S. Appl. No. 11/098,266; Nov. 29, 2006; USPTO; Alexandria, Virgina; All Pages.
LDR Medical, by its attorneys; Reply to Office Action in U.S. Appl. No. 11/098,266; Aug. 22, 2006; USPTO; Alexandria, Virgina; All Pages.
U.S. Patent & Trademark Office; Office Action in U.S. Appl. No. 11/098,266; Mar. 22, 2006; USPTO; Alexandria, Virgina; All Pages.
U.S. Patent & Trademark Office; Notice of Allowance in U.S. Appl. No. 12/391,086; Apr. 15, 2011; USPTO; Alexandria, Virgina; All Pages.
LDR Medical by its attorneys; Reply to Office Action in U.S. Appl. No. 12/391,086; Jan. 31, 2011; USPTO; Alexandria, Virgina; All Pages.
U.S. Patent & Trademark Office; Office Action in U.S. Appl. No. 12/391,086; Jul. 29, 2010; USPTO; Alexandria, Virgina; All Pages.
U.S. Patent & Trademark Office; Office Action in U.S. Appl. No. 13/215,123; Nov. 18, 2013; USPTO; Alexandria, Virgina; All Pages.
LDR Medical, by its attorneys; Reply to Office Action in U.S. Appl. No. 13/215,123; Nov. 11, 2013; USPTO; Alexandria, Virgina; All Pages.
LDR Medical, by its attorneys; Reply to Office Action in U.S. Appl. No. 13/215,123; Oct. 24, 2013; USPTO; Alexandria, Virgina; All Pages.
U.S. Patent & Trademark Office; Office Action in U.S. Appl. No. 13/215,123; May 24, 2013; USPTO; Alexandria, Virgina; All Pages.
LDR Medical, by its attorneys; Reply to Office Action in U.S. Appl. No. 13/215,123; Mar. 20, 2013; USPTO; Alexandria, Virgina; All Pages.
LDR Medical, by its attorneys; Terminal Disclaimer in U.S. Appl. No. 13/215,123; Mar. 20, 2013; USPTO; Alexandria, Virgina; All Pages.
U.S. Patent & Trademark Office; Office Action in U.S. Appl. No. 13/215,123; Nov. 20, 2012; USPTO; Alexandria, Virgina; All Pages.
U.S. Patent & Trademark Office; Notice of Allowance in U.S. Appl. No. 12/360,050; Aug. 2, 2012; USPTO; Alexandria, Virgina; All Pages.

(56) References Cited

OTHER PUBLICATIONS

U.S. Patent & Trademark Office; Notice of Allowance in U.S. Appl. No. 12/360,050; Jul. 6, 2012; USPTO; Alexandria, Virgina; All Pages.
U.S. Patent & Trademark Office; Notice of Allowance in U.S. Appl. No. 12/360,050; May 18, 2012; USPTO; Alexandria, Virgina; All Pages.
U.S. Patent & Trademark Office; Notice of Allowance in U.S. Appl. No. 12/360,050; Mar. 26, 2012; USPTO; Alexandria, Virgina; All Pages.
LDR Medical, by its attorneys; Reply to Office Action in U.S. Appl. No. 12/360,050; Mar. 6, 2012; USPTO; Alexandria, Virgina; All Pages.
U.S. Patent & Trademark Office; Office Action in U.S. Appl. No. 12/360,050; Sep. 6, 2011; USPTO; Alexandria, Virgina; All Pages.
LDR Medical, by its attorneys; Reply to Office Action in U.S. Appl. No. 12/360,050; Jun. 16, 2011; USPTO; Alexandria, Virgina; All Pages.
U.S. Patent & Trademark Office; Office Action in U.S. Appl. No. 12/360,050; Dec. 17, 2010; USPTO; Alexandria, Virgina; All Pages.
U.S. Patent & Trademark Office; Office Action in U.S. Appl. No. 13/603,043; Nov. 21, 2013; USPTO; Alexandria, Virgina; All Pages.
LDR Medical, by its attorneys; Reply to Office Action in U.S. Appl. No. 13/603,043; Oct. 9, 2013; USPTO; Alexandria, Virgina; All Pages.
U.S. Patent & Trademark Office; Office Action in U.S. Appl. No. 13/603,043; Apr. 9, 2013; USPTO; Alexandria, Virgina; All Pages.
U.S. Patent & Trademark Office; Notice of Allowance in U.S. Appl. No. 11/180,868; Jul. 31, 2009; USPTO; Alexandria, Virgina; All Pages.
U.S. Patent & Trademark Office; Notice of Allowance in U.S. Appl. No. 11/180,868; Jul. 17, 2009; USPTO; Alexandria, Virgina; All Pages.
LDR Medical, by its attorneys; Reply to Office Action in U.S. Appl. No. 11/180,868; Mar. 5, 2009; USPTO; Alexandria, Virgina; All Pages.
U.S. Patent & Trademark Office; Office Action in U.S. Appl. No. 11/180,868; Nov. 5, 2008; USPTO; Alexandria, Virgina; All Pages.
LDR Medical, by its attorneys; Reply to Office Action in U.S. Appl. No. 11/180,868; Jul. 21, 2008; USPTO; Alexandria, Virgina; All Pages.
U.S. Patent & Trademark Office; Office Action in U.S. Appl. No. 11/180,868; Jan. 22, 2008; USPTO; Alexandria, Virgina; All Pages.
U.S. Patent & Trademark Office; Notice of Allowance in U.S. Appl. No. 12/435,955; Jan. 16, 2013; USPTO; Alexandria, Virgina; All Pages.
LDR Medical, by its attorneys; Reply to Office Action in U.S. Appl. No. 12/435,955; Dec. 24, 2012; USPTO; Alexandria, Virgina; All Pages.
U.S. Patent & Trademark Office; Office Action in U.S. Appl. No. 12/435,955; Jul. 23, 2012; USPTO; Alexandria, Virgina; All Pages.
LDR Medical, by its attorneys; Reply to Office Action in U.S. Appl. No. 12/435,955; Apr. 11, 2012; USPTO; Alexandria, Virgina; All Pages.
U.S. Patent & Trademark Office; Office Action in U.S. Appl. No. 12/435,955; Oct. 11, 2011; USPTO; Alexandria, Virgina; All Pages.
U.S. Patent & Trademark Office; Office Action in U.S. Appl. No. 13/892,933; Jan. 2, 2014; USPTO; Alexandria, Virgina; All Pages.
U.S. Patent & Trademark Office; Notice of Allowance in U.S. Appl. No. 11/341,007; Jul. 26, 2010; USPTO; Alexandria, Virgina; All Pages.
LDR Medical, by its attorneys; Reply to Office Action in U.S. Appl. No. 11/341,007; Jun. 17, 2010; USPTO; Alexandria, Virgina; All Pages.
U.S. Patent & Trademark Office; Office Action in U.S. Appl. No. 11/341,007; Dec. 17, 2009; USPTO; Alexandria, Virgina; All Pages.
LDR Medical, by its attorneys; Reply to Office Action in U.S. Appl. No. 11/341,007; Oct. 13, 2009; USPTO; Alexandria, Virgina; All Pages.
U.S. Patent & Trademark Office; Office Action in U.S. Appl. No. 11/341,007; Apr. 13, 2009; USPTO; Alexandria, Virgina; All Pages.
U.S. Patent & Trademark Office; Office Action in U.S. Appl. No. 12/955,898; Mar. 3, 2014; USPTO; Alexandria, Virgina; All Pages.
LDR Medical, by its attorneys; Reply to Office Action in U.S. Appl. No. 12/955,898; Jul. 10, 2013; USPTO; Alexandria, Virgina; All Pages.
U.S. Patent & Trademark Office; Office Action in U.S. Appl. No. 12/955,898; Jan. 10, 2013; USPTO; Alexandria, Virgina; All Pages.
LDR Medical, by its attorneys; Reply to Office Action in U.S. Appl. No. 12/955,898; Dec. 3, 2012; USPTO; Alexandria, Virgina; All Pages.
U.S. Patent & Trademark Office; Office Action in U.S. Appl. No. 12/955,898; Jun. 1, 2012; USPTO; Alexandria, Virgina; All Pages.
LDR Medical, by its attorneys; Reply to Office Action in U.S. Appl. No. 12/955,898; Apr. 19, 2012; USPTO; Alexandria, Virgina; All Pages.
U.S. Patent & Trademark Office; Office Action in U.S. Appl. No. 12/955,898; Mar. 19, 2012; USPTO; Alexandria, Virgina; All Pages.
LDR Medical, by its attorneys; Reply Brief in U.S. Appl. No. 11/362,253; Aug. 20, 2012; USPTO; Alexandria, Virgina; All Pages.
U.S. Patent & Trademark Office; Examiners Answer to Appeal Brief in U.S. Appl. No. 11/362,253; Jun. 20, 2012; USPTO; Alexandria, Virgina; All Pages.
LDR Medical, by its attorneys; Appeal Brief in U.S. Appl. No. 11/362,253; Apr. 9, 2012; USPTO; Alexandria, Virgina; All Pages.
U.S. Patent & Trademark Office; Office Action in U.S. Appl. No. 11/362,253; Mar. 8, 2011; USPTO; Alexandria, Virgina; All Pages.
LDR Medical, by its attorneys; Reply to Office Action in U.S. Appl. No. 11/362,253; Dec. 20, 2010; USPTO; Alexandria, Virgina; All Pages.
U.S. Patent & Trademark Office; Office Action in U.S. Appl. No. 11/362,253; Jun. 18, 2010; USPTO; Alexandria, Virgina; All Pages.
LDR Medical, by its attorneys; Reply to Office Action in U.S. Appl. No. 11/362,253; Apr. 15, 2010; USPTO; Alexandria, Virgina; All Pages.
U.S. Patent & Trademark Office; Office Action in U.S. Appl. No. 11/362,253; Oct. 15, 2009; USPTO; Alexandria, Virgina; All Pages.
LDR Medical, by its attorneys; Reply to Office Action in U.S. Appl. No. 11/362,253; Aug. 18, 2009; USPTO; Alexandria, Virgina; All Pages.
U.S. Patent & Trademark Office; Office Action in U.S. Appl. No. 11/362,253; Feb. 18, 2009; USPTO; Alexandria, Virgina; All Pages.
U.S. Patent & Trademark Office; Notice of Allowance in U.S. Appl. No. 13/620,797; Jan. 29, 2014; USPTO; Alexandria, Virgina; All Pages.
LDR Medical, by its attorneys; Reply to Office Action in U.S. Appl. No. 13/620,797; Nov. 5, 2013; USPTO; Alexandria, Virgina; All Pages.
U.S. Patent & Trademark Office; Office Action in U.S. Appl. No. 13/620,797; Jul. 5, 2013; USPTO; Alexandria, Virgina; All Pages.
U.S. Patent & Trademark Office; Notice of Allowance in U.S. Appl. No. 12/134,884; Nov. 1, 2012; USPTO; Alexandria, Virgina; All Pages.
LDR Medical, by its attorneys; Reply to Office Action in U.S. Appl. No. 12/134,884; Jul. 31, 2012; USPTO; Alexandria, Virgina; All Pages.
U.S. Patent & Trademark Office; Office Action in U.S. Appl. No. 12/134,884; Jan. 31, 2012; USPTO; Alexandria, Virgina; All Pages.
U.S. Patent & Trademark Office; Office Action in U.S. Appl. No. 13/520,041; Mar. 20, 2014; USPTO; Alexandria, Virgina; All Pages.
U.S. Patent & Trademark Office; Notice of Allowance in U.S. Appl. No. 11/676,237; Feb. 20, 2013; USPTO; Alexandria, Virgina; All Pages.
LDR Medical, by its attorneys; Reply to Office Action in U.S. Appl. No. 11/676,237; Feb. 6, 2013; USPTO; Alexandria, Virgina; All Pages.
U.S. Patent & Trademark Office; Office Action in U.S. Appl. No. 11/676,237; Nov. 6, 2012; USPTO; Alexandria, Virgina; All Pages.
LDR Medical, by its attorneys; Reply to Office Action in U.S. Appl. No. 11/676,237; Jul. 16, 2012; USPTO; Alexandria, Virgina; All Pages.

(56) References Cited

OTHER PUBLICATIONS

U.S. Patent & Trademark Office; Office Action in U.S. Appl. No. 11/676,237; Feb. 16, 2012; USPTO; Alexandria, Virgina; All Pages.
LDR Medical, by its attorneys; Appeal Brief in U.S. Appl. No. 11/676,237; Oct. 17, 2011; USPTO; Alexandria, Virgina; All Pages.
U.S. Patent & Trademark Office; Office Action in U.S. Appl. No. 11/676,237; Sep. 15, 2010; USPTO; Alexandria, Virgina; All Pages.
LDR Medical, by its attorneys; Reply to Office Action in U.S. Appl. No. 11/676,237; Jun. 18, 2010; USPTO; Alexandria, Virgina; All Pages.
U.S. Patent & Trademark Office; Office Action in U.S. Appl. No. 11/676,237; Dec. 18, 2009; USPTO; Alexandria, Virgina; All Pages.
LDR Medical, by its attorneys; Reply to Office Action in U.S. Appl. No. 11/676,237; Sep. 21, 2009; USPTO; Alexandria, Virgina; All Pages.
U.S. Patent & Trademark Office; Office Action in U.S. Appl. No. 11/676,237; Mar. 20, 2009; USPTO; Alexandria, Virgina; All Pages.
LDR Medical, by its attorneys; Reply to Office Action in U.S. Appl. No. 13/919,704; Jan. 31, 2014; USPTO; Alexandria, Virgina; All Pages.
U.S. Patent & Trademark Office; Office Action in U.S. Appl. No. 13/919,704; Oct. 31, 2013; USPTO; Alexandria, Virgina; All Pages.
LDR Medical, by its attorneys; Interview Summary in U.S. Appl. No. 12/527,373; Jan. 31, 2014; USPTO; Alexandria, Virgina; All Pages.
U.S. Patent & Trademark Office; Notice of Allowance in U.S. Appl. No. 12/527,373; Dec. 24, 2013; USPTO; Alexandria, Virgina; All Pages.
LDR Medical, by its attorneys; Request for Continued Examination in U.S. Appl. No. 12/527,373; Dec. 2, 2013; USPTO; Alexandria, Virgina; All Pages.
U.S. Patent & Trademark Office; Notice of Allowance in U.S. Appl. No. 12/527,373; Aug. 30, 2013; USPTO; Alexandria, Virgina; All Pages.
U.S. Patent & Trademark Office; Interview Summary in U.S. Appl. No. 12/527,373; Aug. 30, 2013; USPTO; Alexandria, Virgina; All Pages.
LDR Medical, by its attorneys; Appeal Brief in U.S. Appl. No. 12/527,373; Apr. 24, 2013; USPTO; Alexandria, Virgina; All Pages.
U.S. Patent & Trademark Office; Office Action in U.S. Appl. No. 12/527,373; Sep. 24, 2012; USPTO; Alexandria, Virgina; All Pages.
LDR Medical, by its attorneys; Reply to Office Action in U.S. Appl. No. 12/527,373; Jun. 21, 2012; USPTO; Alexandria, Virgina; All Pages.
U.S. Patent & Trademark Office; Office Action in U.S. Appl. No. 12/527,373; Dec. 21, 2011; USPTO; Alexandria, Virgina; All Pages.
LDR Medical, by its attorneys; Reply to Office Action in U.S. Appl. No. 13/158,761; Nov. 14, 2013; USPTO; Alexandria, Virgina; All Pages.
U.S. Patent & Trademark Office; Office Action in U.S. Appl. No. 13/158,761; Aug. 14, 2013; USPTO; Alexandria, Virgina; All Pages.
U.S. Patent & Trademark Office; Interview Summary in U.S. Appl. No. 13/158,761; Aug. 1, 2013; USPTO; Alexandria, Virgina; All Pages.
LDR Medical, by its attorneys; Reply to Office Action in U.S. Appl. No. 13/158,761; Jul. 29, 2013; USPTO; Alexandria, Virgina; All Pages.
U.S. Patent & Trademark Office; Office Action in U.S. Appl. No. 13/158,761; Feb. 28, 2013; USPTO; Alexandria, Virgina; All Pages.
LDR Medical, by its attorneys; Reply to Office Action in U.S. Appl. No. 13/158,761; Nov. 19, 2012; USPTO; Alexandria, Virgina; All Pages.
U.S. Patent & Trademark Office; Interview Summary in U.S. Appl. No. 13/158,761; Oct. 31, 2012; USPTO; Alexandria, Virgina; All Pages.
U.S. Patent & Trademark Office; Office Action in U.S. Appl. No. 13/158,761; Oct. 17, 2012; USPTO; Alexandria, Virgina; All Pages.
World Intellectual Property Organization; International Preliminary Report on Patentability for PCT Pub'n No. WO2005104996; Jun. 28, 2006; WIPO; Geneva, Switzerland; all pages.
World Intellectual Property Organization; Written Opinon of the International Searching Authority for PCT Pub'n No. WO2005104996; Sep. 12, 2005; WIPO; Geneva, Switzerland; all pages.
National Institute of Industrial Property (France); Preliminary Search Report in Fench Pub. No. FR2879436; Aug. 11, 2005; National Institute of Industrial Property (France); France; all pages.
World Intellectual Property Organization; International Preliminary Report on Patentability for PCT Pub'n No. WO2006120505; Feb. 22, 2007; WIPO; Geneva, Switzerland; all pages.
World Intellectual Property Organization; International Search Report for PCT Pub'n No. WO2006120505; Aug. 21, 2006; WIPO; Geneva, Switzerland; all pages.
World Intellectual Property Organization; Written Opinon of the International Searching Authority for PCT Pub'n No. WO2006120505; Aug. 21, 2006; WIPO; Geneva, Switzerland; all pages.
National Institute of Industrial Property (France); Preliminary Search Report in Fench Pub. No. FR2887762; Dec. 21, 2005; National Institute of Industrial Property (France); France; all pages.
World Intellectual Property Organization; International Preliminary Report on Patentability for PCT Pub'n No. WO2007000654; Jul. 19, 2007; WIPO; Geneva, Switzerland; all pages.
World Intellectual Property Organization; International Search Report for PCT Pub'n No. WO2007000654; Mar. 14, 2007; WIPO; Geneva, Switzerland; all pages.
World Intellectual Property Organization; Written Opinon of the International Searching Authority for PCT Pub'n No. WO2007000654; Mar. 14, 2007; WIPO; Geneva, Switzerland; all pages.
National Institute of Industrial Property (France); Preliminary Search Report in Fench Pub. No. FR2891135; Jun. 27, 2006; National Institute of Industrial Property (France); France; all pages.
World Intellectual Property Organization; International Preliminary Report on Patentability for PCT Pub'n No. WO2007034310; Aug. 14, 2007; WIPO; Geneva, Switzerland; all pages.
World Intellectual Property Organization; International Search Report for PCT Pub'n No. WO2007034310; Feb. 13, 2007; WIPO; Geneva, Switzerland; all pages.
World Intellectual Property Organization; Written Opinon of the International Searching Authority for PCT Pub'n No. WO2007034310; Feb. 13, 2007; WIPO; Geneva, Switzerland; all pages.
National Institute of Industrial Property (France); Preliminary Search Report in Fench Pub. No. FR2893838; Aug. 4, 2006; National Institute of Industrial Property (France); France; all pages.
World Intellectual Property Organization; International Preliminary Report on Patentability for PCT Pub'n No. WO2007063398; Nov. 12, 2007; WIPO; Geneva, Switzerland; all pages.
World Intellectual Property Organization; International Search Report for PCT Pub'n No. WO2007063398; Jul. 13, 2007; WIPO; Geneva, Switzerland; all pages.
World Intellectual Property Organization; Written Opinon of the International Searching Authority for PCT Pub'n No. WO2007063398; Jul. 13, 2007; WIPO; Geneva, Switzerland; all pages.
National Institute of Industrial Property (France); Preliminary Search Report in Fench Pub. No. FR2916956; Jan. 30, 2008; National Institute of Industrial Property (France); France; all pages.
World Intellectual Property Organization; International Preliminary Report on Patentability for PCT Pub'n No. WO2008149223; Aug. 5, 2009; WIPO; Geneva, Switzerland; all pages.
World Intellectual Property Organization; International Search Report for PCT Pub'n No. WO2008149223; Oct. 31, 2008; WIPO; Geneva, Switzerland; all pages.
World Intellectual Property Organization; Written Opinon of the International Searching Authority for PCT Pub'n No. WO2008149223; Oct. 31, 2008; WIPO; Geneva, Switzerland; all pages.

(56) References Cited

OTHER PUBLICATIONS

World Intellectual Property Organization; International Search Report for PCT Pub'n No. WO2011080535; Jan. 24, 2011; WIPO; Geneva, Switzerland; all pages.

National Institute of Industrial Property (France); Preliminary Search Report in Fench Pub. No. FR2987256; Dec. 5, 2012; National Institute of Industrial Property (France); France; all pages.

World Intellectual Property Organization; International Search Report for PCT Pub'n No. WO2013124453; May 29, 2013; WIPO; Geneva, Switzerland; all pages.

World Intellectual Property Organization; International Preliminary Report on Patentability for PCT Pub'n No. WO2008099277; May 29, 2009; WIPO; Geneva, Switzerland; all pages.

World Intellectual Property Organization; International Search Report for PCT Pub'n No. WO2008099277; Nov. 7, 2008; WIPO; Geneva, Switzerland; all pages.

World Intellectual Property Organization; Written Opinon of the International Searching Authority for PCT Pub'n No. WO2008099277; Nov. 7, 2008; WIPO; Geneva, Switzerland; all pages.

* cited by examiner

INTERVERTEBRAL DISC PROSTHESIS

CROSS REFERENCE TO RELATED APPLICATIONS:

This application claims priority under 35 U.S.C. 119 based on French Patent Application No. 04 01024, filed in FRANCE on Feb. 4, 2004.

TECHNICAL FIELD

The present invention relates to intervertebral disc prostheses.

BACKGROUND OF THE INVENTION

Various types of prostheses are known in the prior art. Numerous prostheses are constituted by a lower plate and an upper plate enclosing a central core. A part of these prostheses enables the upper plate to slide relative to the central core and optionally permits the central core to slide relative to the lower plate. This sliding of the central core relative to the lower plate allows spontaneous positioning of the core in the ideal position to absorb constraints imposed on the prosthesis during movements made by the patient carrying the prosthesis. However, because of the forces from applied constraints, materials utilized and the form of the different pieces constituting the prosthesis, the sliding of the core is often difficult, which causes rapid wear and heightens the risk of ejection of at least a part of the prosthesis to the outside of the spine, and this is not desirable for the patient.

An intervertebral disc prosthesis is provided that allows movement of the different pieces of the prosthesis between one another, but facilitates core sliding.

Intervertebral disc prostheses in accordance with the present invention comprise at least three pieces including a first plate, a second plate and a core that is mobile relative to at least one of the plates. In a preferred embodiment, the core has a curved surface in contact with at least a part of a complementary curved surface of the first plate and a substantially flat surface in contact with at least a part of a substantially flat surface of the second plate, and limit stops situated near the periphery of the second plate and of the core that limit or prevent, without excessive friction, the movements in translation of the core relative to the second plate, along an axis substantially parallel to the substantially flat surfaces, and limit or prevent the movements in rotation of the core relative to the second plate, about an axis substantially perpendicular to the substantially flat surfaces. In a preferred embodiment, the substantially flat surface of the core has at least one dummy hole facilitating sliding of the core relative to the substantially flat surface of the second plate with which it is in contact.

According to another particular feature in an embodiment, the lower surface of the core and the upper surface of the second plate, known as the lower plate, are substantially flat.

According to another particular feature in an embodiment, at least the substantially flat surface of the core is enclosed in a protective shell, whereof the surface in contact with the substantially flat surface of the second plate and with the substantially flat of the core has at least one hole.

According to another particular feature in an embodiment, the protective shell of the core does not cover the limit stops of the core, so as to avoid contact of the protective shell with the limit stop of the second plate.

According to another particular feature in an embodiment, the area of contact of the substantially flat surface of the core or of the protective shell with the substantially flat surface of the second plate and the area of contact of the curved surface of the core with the curved surfaces of the first plate are substantially equal, on both sides of the core.

According to another particular feature in an embodiment, the angle formed by the edges of the hole present at least on the substantially flat surface of the core or of the protective shell of the core is softened to improve the sliding of the core or of the shell on the substantially flat surface of the second plate.

According to another particular feature in an embodiment, the hole present on the substantially flat surface of the core or of the protective shell of the core is prolonged, as far as the periphery of this substantially flat surface, by grooves forming channels via which the interstitial liquid from surrounding tissue can play a lubricating role to improve the sliding of the core on the substantially flat surface of the second plate, when the prosthesis is in place on the patient.

According to another particular feature in an embodiment, the angle formed by the edges of the grooves prolonging the hole as far as the periphery of the substantially flat surface of the core or of the protective shell of the core is softened to improve the sliding of the core or of the shell on the substantially flat surface of the second plate.

According to another particular feature in an embodiment, the core is made of polyethylene.

According to another particular feature in an embodiment, the protective shell of the core is made of metal.

According to another particular feature in an embodiment, the first and second plates are made of metal.

According to another particular feature in an embodiment, the limit stops consist of male structure of the second plate, cooperating with female structure of the core.

According to another particular feature in an embodiment, the core is mobile relative to the first and/or second plates and that a variable angle between the first and second plates depends on the position of the core, an inclination, in any direction at all, of at least the first plate inducing the displacement of the core between the plates and providing freedom of movement for the patient and, at the same time, helping eliminate the positioning defects of the prosthesis.

According to another particular feature in an embodiment, an angle between the upper surface of the upper plate and the lower surface of the lower plate can be imposed either by the fact that the plane means representing the upper and lower surfaces of the core form an angle, or by the fact that the plane means representing the upper and lower surfaces of the first plate and/or of the second plate form an angle, or by restriction of the movements of the core about a position imposing inclination of at least the first plate.

According to another particular feature in an embodiment, the same plates can be assembled with cores of different thicknesses.

According to another particular feature in the embodiment, at least a part of the surface of the first plate is concave and complementary to the surface of the core with which it is in contact.

According to another particular feature in the embodiment, the dimensions of each male structure are slightly less than those of each female structure so as to permit slight clearance between the core and the second plate.

According to another particular feature in the embodiment, the dimensions of each male structure are substantially the same as those of each female structure so as to prevent any clearance between the core and the second plate.

According to another particular feature in the embodiment, the male structure of the second plate are two contact plates situated opposite one another on two edges of the prosthesis, and the female structure of the core are two recesses.

According to another particular feature in the embodiment, the male structure of the second plate are two walls situated opposite one another in the vicinity of two edges of the prosthesis, and in that the female structure of the core are recesses.

According to another particular feature in the embodiment, the male structure of the lower plate are two nibs curved towards the interior of the prosthesis and situated opposite one another on two edges of the prosthesis, and the female structure of the core are two recesses.

According to another particular feature in the embodiment, at least one of the nibs is replaced by a pin equipped with a hole and on which a plate is fixed by means of a dowel penetrating the hole.

According to another particular feature in the embodiment, the lower surface of the lower plate and the upper surface of the upper plate are provided with teeth or notches situated in the vicinity of at least two edges of the prosthesis and oriented so as to prevent sliding of the prosthesis prior to its adhesion to the osseous tissue permitted by a porous biocompatible coating of the surfaces of the plates in contact with the vertebrae.

According to another particular feature in the embodiment, at least the second plate comprises one or more openings in the vicinity of its front side, provided to receive anchoring means of the prosthesis in a vertebra.

According to another particular feature in the embodiment, the openings of the second plate are circular, and in that the anchoring means have the form of a stud.

According to another particular feature in the embodiment, the head of the anchoring means have larger dimensions than the openings of the second plate, the anchoring means being fixed into a vertebra, the second plate is sandwiched in between the head of the anchoring means and said vertebra.

According to another particular feature in the embodiment, the upper plate is bulged on at least a part of its upper surface to adapt to the form of the vertebrae.

Another aim is to propose an insertion device, between two vertebrae, of intervertebral disc prostheses constituted by a lower plate, an upper plate and a mobile core at least relative to the lower plate. It would be advantageous for the prosthesis insertion device between two vertebrae to allow the prosthesis to be kept sterile, to position it facing the opening made by the surgeon between the two vertebrae, to have it enter this opening by translation then to withdraw the device leaving the prosthesis inserted in its opening.

This aim is attained by an insertion device, between two vertebrae, of intervertebral disc prostheses constituted by a first plate, an second plate and a mobile core at least relative to the second plate, characterised in that it comprises a clip whereof the front surface has a form provided to fit the form of the front edge of the prosthesis and whereof at least two edges are equipped with a gripping means.

According to another particular feature in the embodiment, the gripping means present on the clip may be exhibited, for example, as two flexible blades mounted on the lateral edges of the clip and holding the prosthesis by pinching the lateral edges of the upper and lower plates of the prosthesis.

According to another particular feature in the embodiment, the front surface of the clip has a form provided to fit the form of the front edge of the prosthesis, on one hand, owing to its height at least substantially equal to the height of the prosthesis, so as to come into contact with the front edges of each of the plates of the prosthesis and, on the other hand, to at least one groove in at least the median part of the front surface of the clip to likewise come in contact with the front edge of the core which is slightly set back relative to the front edges of the plates.

According to another particular feature in the embodiment, the rear surface of the clip can be pushed by a first end of a rod, known as a guide, equipped with a pusher at its other end and with a limit stop at a variable position along the guide for limiting the length of the sliding of the guide inside a body of a charger equipped with a head in which is arranged a space dimensioned for receiving the prosthesis and the clip, the position of the limit stop on the guide being adjustable such that the prosthesis, held by the clip, exits from the head of the charger and is centred relative to the vertical axis of the two vertebrae between which it must be implanted when the limit stop contacts the body of the charger.

According to another particular feature in the embodiment, the front end of the gripping means of the prosthesis present on at least two edges of the clip is larger than their back end at which the width of the clip is substantially equal to the width of the space in the head of the charger, such that, when the prosthesis and the clip are in the head of the charger, the prosthesis is held firmly by the gripping means of the clip which are then compressed between the prosthesis and the internal wall of the space arranged in the head of the charger and, when the prosthesis exits from the head of the charger, it is held less firmly by the clip, so as to be able to be released therefrom.

BRIEF DESCRIPTION OF FIGURES

Other particular features and advantages of the embodiments of present invention will emerge more clearly from the description hereinbelow, given in reference to the attached drawings, in which.

DESCRIPTION OF PREFERRED EMBODIMENTS

Figure 1A:
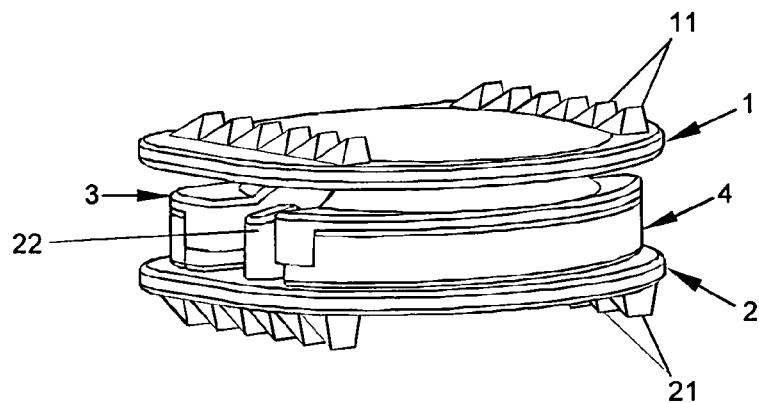
FIG. 1a illustrates a perspective view of a prosthesis according to an embodiment of the invention, viewed from the front.
Figure 1B:
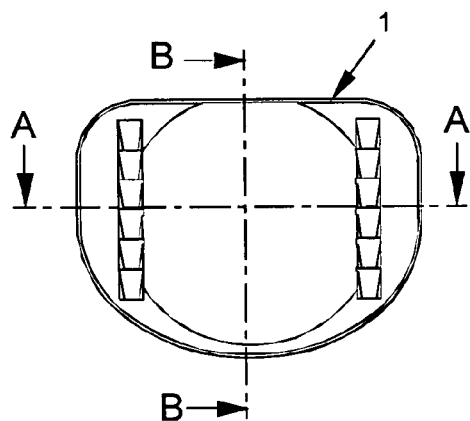
FIG. 1b illustrates a top view of a prosthesis with the planes of section A-A and B-B, respectively of FIGS. 1c and 1d.
Figure 1C:
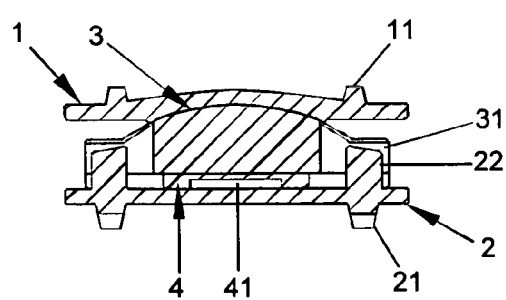
Figure 1D:
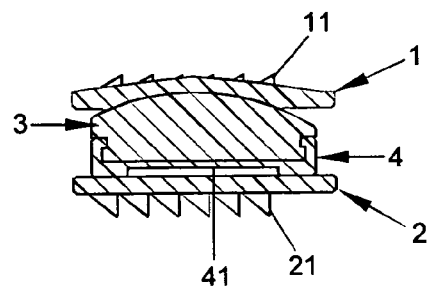

The intervertebral disc prosthesis according to an embodiment of the present invention is comprised of a first plate (1) articulated relative to a second plate (2) by means of a core (3), as evident in particular in FIGS. 1a, 1c and 1d. In the following description, the first plate (1) is called the upper plate and the second plate (2) is called the lower plate, according to the orientation given to the prosthesis shown in the drawings. Those of skill will recognize after appreciating this disclosure that the prosthesis could be inversely oriented between the vertebrae, so that the first plate (1) would be the lower plate and the second plate (2) would be the upper plate. An advantage of the prosthesis according to the present invention is that it comprises simple pieces which can be dimensioned so that the prosthesis is placed on the cervical spine.

The core (3) is of less thickness (for example 3 mm in a preferred embodiment) for a cervical prosthesis or thicker (for example 15 mm in a preferred embodiment) for a lumbar prosthesis.

Figure 4A:
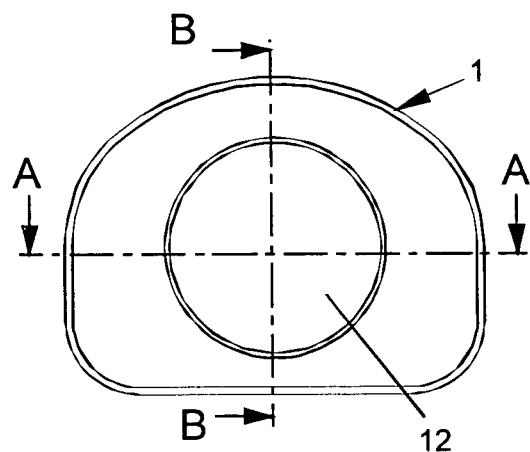
FIG. 4a illustrates a bottom view of the upper plate of the prosthesis, with the planes of sections A-A and B-B, respectively of FIGS. 4c and 4d.
Figure 4B:
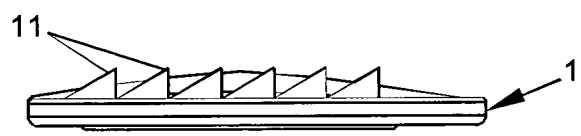
FIG. 4b illustrates a side view of the upper plate of the intervertebral disc prosthesis according to an embodiment of the invention.
Figure 4C:
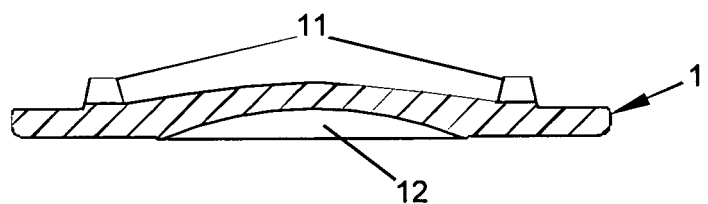
Figure 4D:
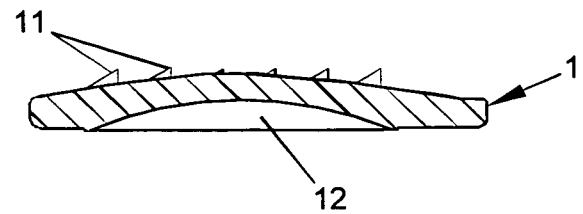
Figure 5A:
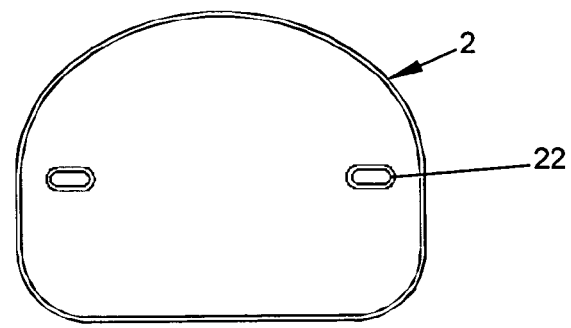
FIG. 5a illustrates a top view of the lower plate of the prosthesis.
Figure 5B:
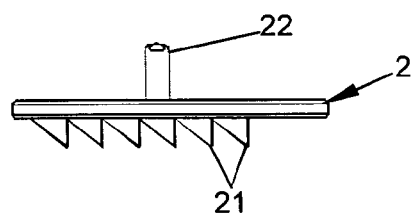
FIGS. 5b and 5c illustrate respectively side views and front views of the lower plate of the prosthesis and FIGS. 5d and 5e illustrate, in perspective, respectively, a top view and a bottom view of the lower plate of the intervertebral disc prosthesis according to an embodiment of the invention.
Figure 5C:
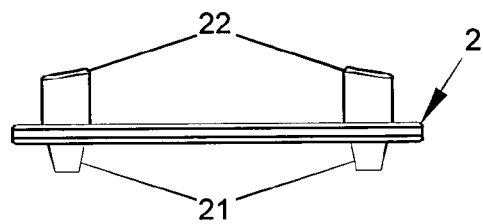
Figure 5D:
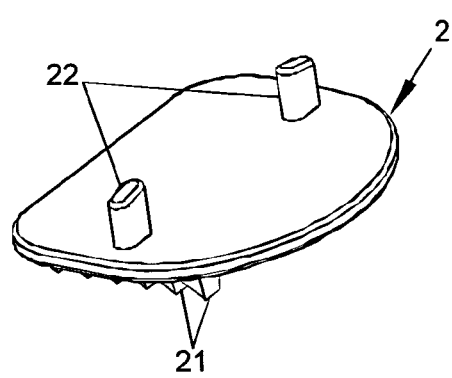
Figure 5E:
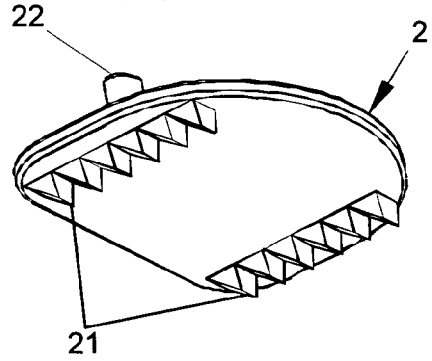
Figure 6A:
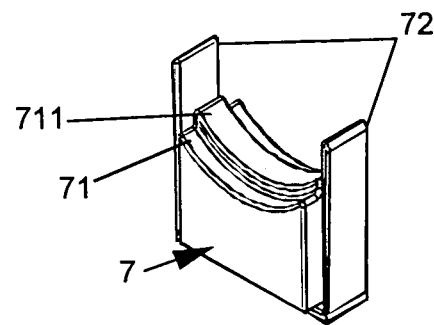
FIG. 6a illustrates a view in perspective of the clip of the insertion device of intervertebral disc prostheses between two vertebrae.
Figure 6B:
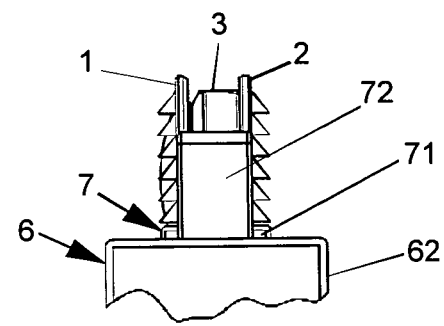
FIGS. 6b and 6c illustrate a partial profile and top view, respectively, of the head of the charger of the prosthesis insertion device between two vertebrae, with the prosthesis held by the clip in extended position.
Figure 6C:
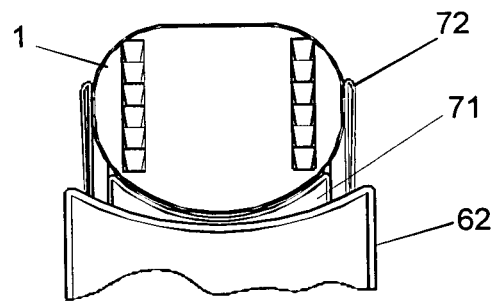
Figure 6D:
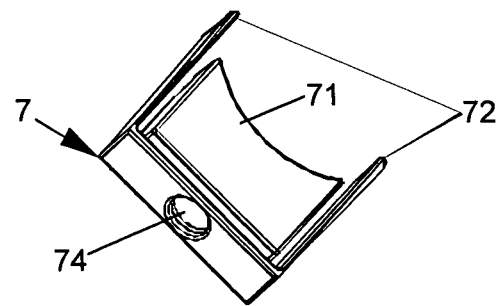
FIG. 6d illustrates a view in perspective of the clip of the insertion device of intervertebral disc prostheses between two vertebrae.
Figure 7A:
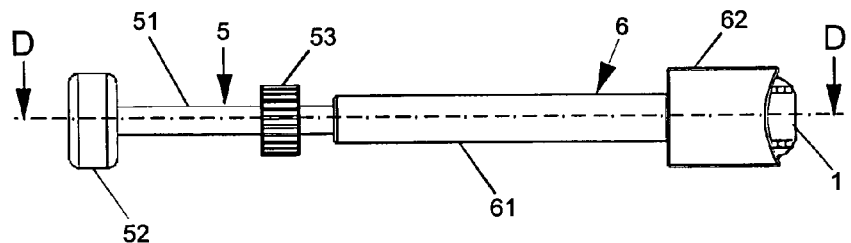
FIG. 7a illustrates a top view of the complete prosthesis insertion device between two vertebrae when the prosthesis held by the clip is retracted into the head of a charger.
Figure 7B:
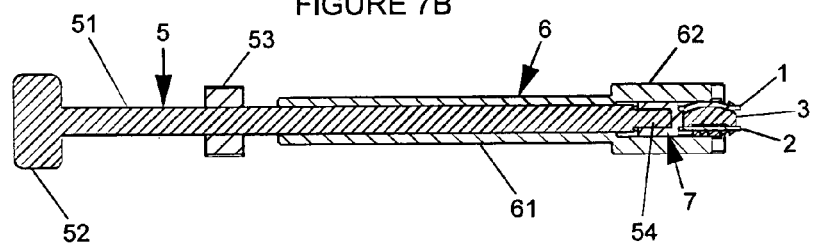
FIG. 7b illustrates it according to the section plan D-D of FIG. 7a, FIG. 7c illustrates a top view of the complete prosthesis insertion device between two vertebrae when the prosthesis held by the clip is extended from the head of the charger
Figure 7C:
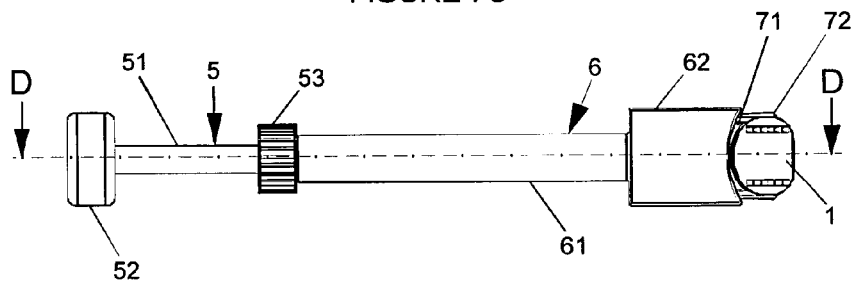
FIG. 7d illustrates it according to the section plan D-D of FIG. 7c.
Figure 7D:
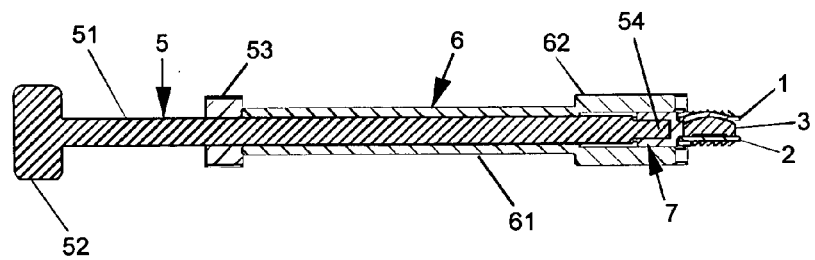

In another embodiment, a part of the upper surface of the upper plate (1) is bulged, as shown in FIGS. 4b to 4d, so as to better adapt to the vertebra on which the prosthesis is intended to be placed, the lower surface of the vertebrae being hollow. The bulged part of the upper plate (1) is then situated in the front part of the upper plate, as shown in particular in FIG. 4d. The lower plate (2) is substantially flat and in preferred embodiments, its lower surface has no requirement to be bulged or hollow, since the upper surface of the vertebrae is substantially flat.

In the embodiment of FIGS. 1a to 1d, 4b to 4d and 5b to 5e, the upper surface of the upper plate (1) and the lower surface of the lower plate (2) are provided with teeth or notches (11, 21) situated in the region of at least two edges of the prosthesis. These notches (11, 21), oriented so as to prevent sliding of the prosthesis, serve as anchors for the prosthesis at times when the osseous tissue adheres to these surfaces of the plates in contact with the vertebrae. In fact, the osseous tissue, in the few weeks following surgical intervention for implanting the prosthesis, will invade the surfaces with which it is in contact. A porous biocompatible coating is provided on these surfaces to allow adhesion of the osseous tissue and its definitive fusion with the prosthesis.

In another embodiment, the lower surface of the core (3) is enclosed by a protective shell (4) of the core. This protective shell (4) is, for example, drilled, in the centre of its lower surface, with at least one hole (41), for example a dummy, which improves sliding on the upper surface of the lower plate (2). In a simpler variant embodiment, in the absence of this protective shell (4), it is the lower surface of the core (3) which, for example, will be pierced by a dummy hole in its centre. The core alone will then have substantially the same appearance as the ensemble made up by the core (3) and its protective shell (4), such as in the embodiment described hereinafter and illustrated in FIGS. 2a to 2e. The size and form, for example oval, of the hole (41) through the core (3) or the protective shell (4) are adapted to the size and form of the core or of the protective shell. The hole will have been made so that the angles formed by its edges (411) are softened to reduce friction on the lower plate. This hole (41) of adapted dimensions can of course be replaced by a plurality of smaller holes, whereof the extent will be adapted to the size and form of the core or of the protective shell. For example, a multitude of concave minuscule alveoli could be arranged on the lower surface of the core or of the protective shell.

In a variant embodiment the dummy hole (41) present at least on the lower surface of the core (3) or of the protective shell (4) of the core is prolonged by grooves (410) which extend as far as the periphery of this lower surface. These grooves (410) thus form channels via which interstitial liquid from surrounding tissue can slide between the lower surface of the core (3) or of the protective shell (4) and play a lubricating role to improve sliding of the core (3) on the upper surface of the lower plate (2).

The hole (41) and the eventual grooves (410) may be such that the area of contact between the lower surface of the core (3) and the upper surface of the lower plate (2) is substantially equal to the area of contact between the upper surface of the core (3) and the lower surface of the upper plate (1). The constraints applied to the prosthesis will thus be absorbed equally by both surfaces of the core (3) in this embodiment, which will allow reducing frictions and improving the life duration of the core by optimizing the displacement of the core (3) relative to the plates (1, 2)

Figure 2A:
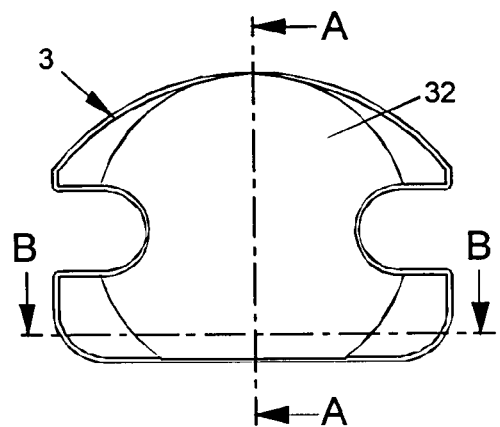
FIG. 2a illustrates a top view of the core equipped with its protective shell in an embodiment of the invention, with the planes of sections A-A and B-B, respectively of FIGS. 2b and 2c.
Figure 2B:
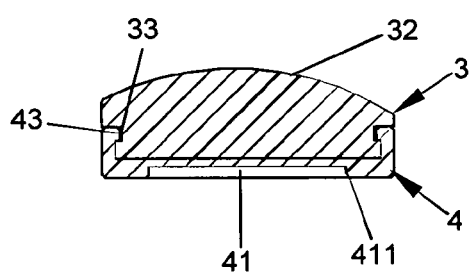
FIGS. 2d and 2e illustrate, in perspective, respectively, a top view and a bottom view of the core equipped with its protective shell.
Figure 2C:
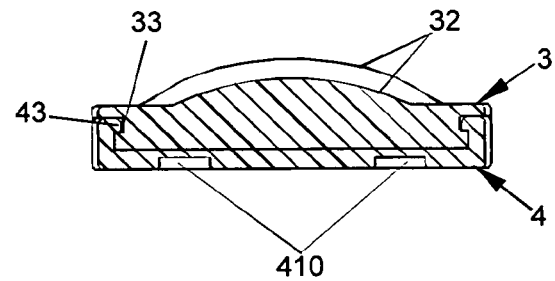
Figure 2D:
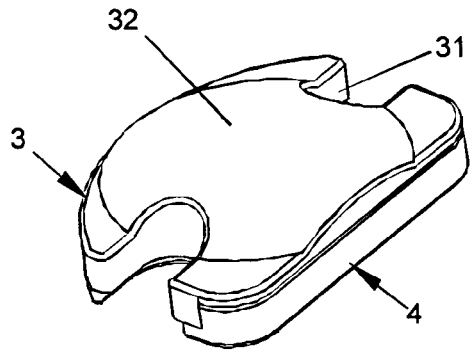
Figure 2E:
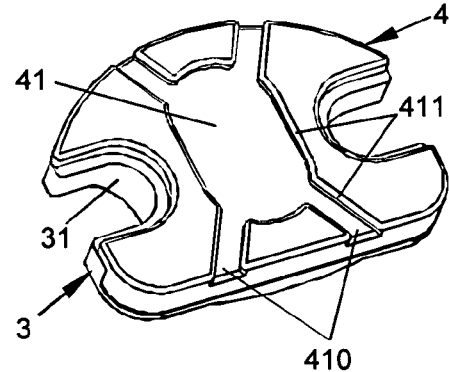
Figure 3A:
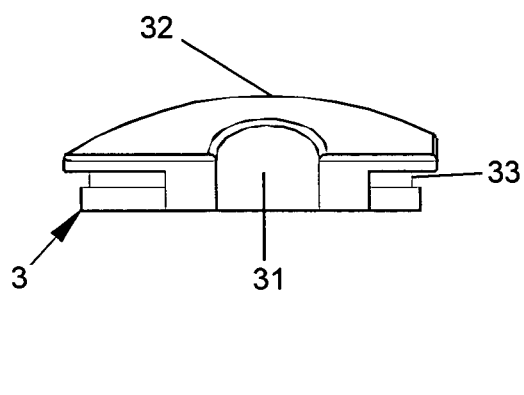
FIGS. 3a and 3b illustrate respectively a profile view and a top view in perspective of a core deprived of a protective shell in an embodiment of the invention.
Figure 3B:
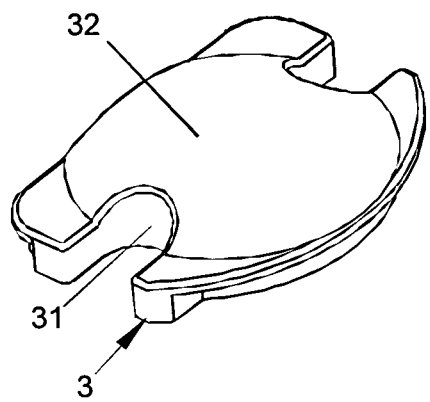
Figure 3C:
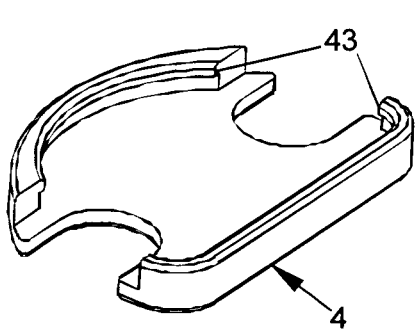
FIGS. 3c and 3d illustrate, in perspective, respectively, a top view and a bottom view of the protective shell of the core according to an embodiment of the invention.
Figure 3D:
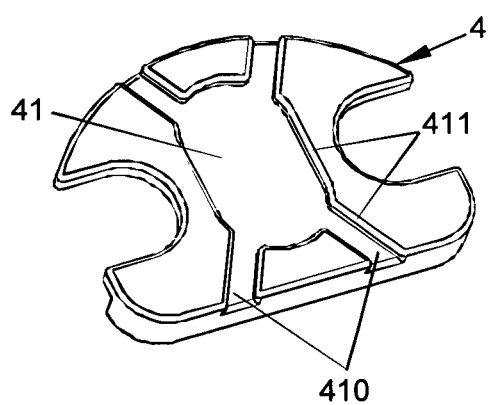

In the embodiment where the lower surface of the core (3) is enclosed by a protective shell (4), the lower part of the core may be narrower than its upper part, such that once the protective shell (4) is mounted on the lower part, the core has substantially homogeneous dimensions, as shown in FIGS. 2a to 2e. On the circumference of the core, substantially at the centre of its thickness, a groove (33), shown in FIGS. 2b, 2c and 3a, complementary to a groove (43), illustrated in FIGS. 2b, 2c and 3c, present on the internal part of the edges of the protective shell (4), provides cohesion of the ensemble made up by the core (3) and its protective shell (4). The core (3) will then be simply encased in the protective shell (4) when the prosthesis is mounted.

The core (3) in this embodiment has, on at least one part of its upper surface, a convex part (32), evident particularly in FIGS. 2a to 2d, 3a and 3b, complementary to a concave part (12) of the upper plate (1), evident particularly in FIGS. 4a, 4c and 4d. This concave part (12) permits inclination of the upper plate (1) when the patient wearing the prosthesis bends over. The lower surface of the core (3) or of the protective shell (4) and the upper surface of the lower plate (2) could be plane, or substantially flat, so as to permit clearance of the core (3) relative to the lower plate (2), both in translation according to an axis substantially parallel to the lower plate (2), and in rotation about an axis substantially perpendicular to the lower plate (2). During movements made by the patient wearing the prosthesis, this inclination of the upper plate (1) and this clearance of the core will allow displacement of the core (3) towards the ideal position to absorb the constraints applied to the prosthesis. The movement between the upper plate (1) and the core (3), as well as the clearance of the core (3) relative to the lower plate (2) thus allow the patient to move, and, optionally, to eliminate the defects of positioning the prosthesis. This clearance likewise has the advantage of preventing premature wear due to the constraints applied to the prosthesis. The dummy hole (41) bored in the lower surface of the core (3) or of the protective shell (4) will help improve sliding of the core on the upper surface of the lower plate, so that the core can find the ideal position for absorbing the constraints imposed on the prosthesis as fast and as easily as possible. For good absorption of the constraints, the core (3) could, for example, be made of polyethylene, or other materials that are compressible and may simulate physical properties of natural intervertebral discs such as elasticity, for example.

According to an embodiment of the invention, the lower surface of a core (3) made of compressible material could be enclosed by a metallic protective shell (4), permitting better sliding on the lower metallic plate (2) and reduction in creep of the compressible material. The sliding of the core will be improved by a hole (41), for example a dummy, bored in the lower surface of the protective shell (4).

In the embodiment of FIGS. 1a, 1c and 5a to 5e the lower plate (2) comprises two contact plates (22) situated opposite one another on two edges of the lower plate (2), at each lateral sides of the lower plate (2). Each contact plate (22) comprises male structure of the lower plate (2) and can penetrate female structure of the core, constituted in this embodiment by a recess (31) of the core (3) on two of its edges. In the embodiment shown in these figures, the dimensions of each recess (31) of the core (3) are slightly greater than those of each nib (22) of the lower plate (2) so as to limit clearance of the core (3) relative to the lower plate (2), both in translation along an axis substantially parallel to the lower plate (2), and in rotation about an axis substantially perpendicular to the lower plate (2).

In the embodiment where a core (3) made of compressible material is provided with a protective metallic shell (4) sliding on a lower metallic plate, the protective shell could be in an adapted form so that it is not in contact with a metallic limit stop of the lower plate. Such a result can be obtained, for example, thanks to the fact that the edges of the protective shell (4) are slightly offset from the limit stops of the core. This variant embodiment can prove necessary since, in a living organism, it is preferable to avoid the shocks between two metallic materials, which risk projecting metallic particles into the surrounding tissue and causing complications.

In a variant embodiment not shown, the dimensions of each recess (31) of the core (3) are substantially the same as those of each nib (22) of the lower plate (2), so as to avoid any clearance of the core (3) relative to the lower plate (2), both in translation and in rotation. In the latter case, the only permitted movement of the prosthesis is that of the upper plate (1) relative to the core (3).

In a variant embodiment not shown, the contact plates (22) are replaced by nibs curved towards the interior of the prosthesis, above the edges of the core (3), so as to prevent the core from being raised. In another variant, one of the nibs is replaced by a contact plate (or pin) equipped with a hole in which, for example, a dowel fixes a plate (or hasp). The ensemble made up by the hasp fixed on the contact plate will have the same form as the nib of the opposite side and will fulfil the same function with the added advantage of facilitating mounting of the different pieces of the prosthesis. In a variant embodiment, the two nibs are each replaced by a contact plate to which a hasp is fixed.

In another variant embodiment not shown, the contact plates (22) of the lower plate (2) are replaced by half dog points. The core (3), by way of complement, does not comprise recesses (31), but two wells under its lower surface. The dimensions of the half dog points of the lower plate (2) and of the wells of the core (3) will be adapted according to the desired result, by choice, of slight clearance of the core in translation and in rotation or any clearance.

In another embodiment not shown, the contact plates (22) of the lower plate (2) are replaced by walls, positioned opposite one another, in the vicinity of two substantially parallel edges of the lower plate, but more towards the interior of the prosthesis than the contact plates (22). The core (3) comprises recesses complementary to the walls. The dimensions of each recess of the core of this embodiment are, either slightly greater, or substantially the same as those of each wall of the lower plate, so as to allow or not slight clearance in translation and in rotation.

In yet another embodiment not shown, the female cooperation means are situated on the lower plate (2) and the male cooperation means on the core (3).

An intervertebral disc prosthesis according to many embodiments of the present invention help to correct the defects of lordosis. The presence of an acute angle, for example of between 0° and 15°, in the postero-anterior direction, between the upper plate (1) and the lower plate (2) of the prosthesis could be desired. To adjust the angle necessary as a function of the patient, it suffices to select a core (3) with an appropriate angle between the average plane representing its upper surface and the plane passing through its lower surface. Such an angle could likewise be obtained by making an upper plate, including the plane means representing its lower and upper surfaces forming an angle. Another possibility involves the lower plate whereof the plane means representing its lower and upper surfaces form an angle. Another possibility consists of a position of the core slightly offset to the rear or the front relative to the centre of the prosthesis including the plates which will then form an angle. This slightly offset position of the core can, for example, be maintained due to adjustable positioning of the male and female limit stops.

In the event where the male structure or stop in the vicinity of the edges of the core (i.e., near the periphery of the core) and the female structure or stops are situated in the vicinity of the edges of the lower plate (i.e., near the periphery of the lower plate), a lordosis core (by the fact that if forms an acute angle in the postero-anterior direction) can then be made solid with the plate by a projection penetrating a cavity or opening in the lower plate. If the surgeon wants lordosis determined for a patient, he will select a core (3) which cannot have any clearance relative to the lower plate (2). However, if he only wants the lordosis to remain within a range of values, he will select a core which can have slight clearance in translation and in rotation relative to the lower plate (2), but about a position imposing slight permanent inclination of at least one of the plates.

The intervertebral disc prosthesis according to a variety of embodiments of the present invention can, in variant embodiments, be anchored solidly, from when implanted, in the vertebral column to prevent the prosthesis from migrating under the effect of the resulting transversal of the force exerted by the vertebral column on the prosthesis in place, an important consideration in lordosis. In this case, the lower plate (2) comprises one or more openings situated in the vicinity of the rear side of the prosthesis, receiving anchors of a variety of types.

Therefore, in a variant embodiment, the openings in the lower plate (2) are circular and the anchors preferably have the shape of studs, with a head having a size greater than that of the openings to allow the lower plate (2) to be sandwiched between the head of the anchors and the vertebra on which the prosthesis is anchored. For greater security, the openings could be made such that the anchors and the lower plate form an angle of less than or equal to 90°.

Intervertebral disc prostheses are typically not easy to implant in the patient. This difficulty is exacerbated by the fact of the relative mobility of the pieces of the prostheses. It is thus preferred to associate these prostheses with a device allowing it to be held and inserted between the vertebrae. Such a device according to an embodiment of the present invention is made up of a clip (7) whereof the front surface (71) has a shape provided to fit the form of the front edge of the prosthesis. This clip (7) has a fitting on its front that grips (72) the prosthesis. These gripping means (72) can, for example, be two (72) flexible blades mounted on the lateral edges of the clip and can hold the prosthesis by pinching the lateral edges of the upper and lower plates of the prosthesis. The front surface (71) of the clip (7) has preferably, for example, a height at least substantially equal to the height of the prosthesis, so as to come into contact with the front edges of each of the plates of the prosthesis.

In an embodiment of the invention, a groove (711) is present in the median part of the front surface (71) of the clip (7) so as to come into contact with the front edge of the core, slightly set back relative to the front edges of the plates. There can of course be several grooves fitting the shape of the prosthesis. The front surface (71) of the clip (7) provided with the groove (711) thus fits the form of the front edge of the prosthesis when in contact with the three elements making up the prosthesis. The clip thus helps hold the prosthesis and push it homogeneously towards its opening between two vertebrae. This clip (7) is provided to hold the prosthesis and to be inserted into a charger (6) (or loader). This charger (6) has a head (62) in which a space is arranged to receive the clip holding the prosthesis and a body (61) provided to slide about a rod, called a guide (5). The rear surface of the clip (7) can be provided with a hole in its centre, provided to insert an end (54) of the guide (5) so that the guide (5) can hold and push the clip (7). The guide (5) is equipped with a pusher (52) at its other end, which will help push the clip and the prosthesis out of the head (62) of the charger (6) by having the guide (5) slide in the body (61) of the charger (6). An adjustable stop is mounted on the guide (5). For example, a threaded ring (53) is screwed around the guide. This ring serves as a stop (53) to the guide when it slides in the body (61) of the charger (6). The position of the stop (53) will be adjusted, as a function of the size of the vertebra, so that when the stop (53) of the guide (5) comes into contact with the body (61) of the charger (6), the end (54) of the guide (5) will have pushed the clip (7) as far as a position where the prosthesis, held by the flexible blades (72) of the clip, is now out of the head (62) of the charger (6) and centred relative to the axis of the vertebral column.

In an embodiment of the prosthesis according to the invention, as described earlier, the upper (1) and lower (2) plates are provided with anchors as such teeth or notches (11 and 21) for example, on their surface in contact with the vertebrae. These anchors or notches (11, 21) are oriented so as to oppose displacement of the prosthesis in the direction of withdrawal of the clip (7), once the prosthesis is entered in its opening between two vertebrae, made in advance by the surgeon. These notches (11, 21) are thus oriented so as to allow the prosthesis to return to its opening but not come out when the surgeon pulls back the clip (7) holding the prosthesis. On the other hand, the front end of the gripping means (72) of the prosthesis is larger (thicker) than their back end. The width of the clip at its back end is substantially equal to (or slightly smaller than) the width of the space in the head (62) of the charger (6). Thanks to these substantially equal dimensions of the space inside the head (62) of the charger (6) and of the prosthesis and the clip (7), when both the latter are in the head (62) of the charger (6), the prosthesis is solidly held by the flexible blades (72) of the clip (7) whereof the front ends are compressed between the prosthesis and the internal wall of the space made in the head (62) of the charger (6). When the surgeon presses on or strikes the pusher (52) of the guide, the prosthesis exits from the head (62) of the charger and it is held less firmly by the clip (7) since the back ends of the flexible blades (72) are less compressed than were the front ends. The prosthesis could then be released from the clip by pulling back the insertion device, owing to the presence of the notches on the lower and upper plates, allowing the prosthesis to remain in its opening between the two vertebrae.

The present invention allows embodiments in numerous other specific forms without departing from the spirit of the invention. As a consequence, the present embodiments must be considered by way of illustration only, and can be modified within the scope defined by the range of the attached claims, and thus, the invention should be.

Although the present invention has been described in detail, it will be apparent to those skilled in the art that many embodiments taking a variety of specific forms and reflecting changes, substitutions and alterations can be made without departing from the spirit and scope of the invention. Therefore, the described embodiments illustrate but do not restrict the scope of the claims.

The invention claimed is:

1. An intervertebral disc prosthesis comprising at least three pieces including a first plate, a second plate and a core mobile at least relative to one of the plates the core having a curved surface in contact with at least a part of a complementary curved surface of the first plate and a substantially flat surface in contact with at least a part of a substantially flat surface of the second plate, and at least one dummy hole disposed in the substantially flat surface of the core and remaining unobstructed by any protrusion from the substantially flat surface of the second plate, thus facilitating sliding of the core relative to the substantially flat surface of the second plate with which it is in contact.

2. The intervertebral disc prosthesis as claimed in claim 1, in which at least the substantially flat surfaces are the lower surface of the core and the upper surface of the second plate, known as lower plate.

3. The intervertebral disc prosthesis as claimed in claim 1, in which the area of contact of the substantially flat surface of the core with the substantially flat surface of the second plate and the area of contact of the curved surface of the core with the curved surfaces of the first plate are substantially equal, on both sides of the core.

4. The intervertebral disc prosthesis as claimed in claim 1, in which the edges of the hole present at least on the substantially flat surface of the core form an angle, which is softened to improve the sliding of the core or of the shell on the substantially flat surface of the second plate.

5. The intervertebral disc prosthesis as claimed in claim 1, in which the hole present on the substantially flat surface of the core is prolonged, as far as the periphery of this substantially flat surface, by grooves forming channels via which the interstitial liquid from surrounding tissue can play a lubricating role to improve the sliding of the core on the substantially flat surface of the second plate, when the prosthesis is in place on the patient.

6. The intervertebral disc prosthesis as claimed in claim 5, in which the angle formed by the edges of the grooves prolonging the hole as far as the periphery of the substantially flat surface of the core is softened to improve the sliding of the core or of the shell on the substantially flat surface of the second plate.

7. The intervertebral disc prosthesis as claimed in claim 1, in which the core is made of polyethylene.

8. The intervertebral disc prosthesis as claimed as claimed in claim 1, in which the first and second plates are made of metal.

9. The intervertebral disc prosthesis as claimed in claim 1, in which the core is mobile relative to the first and/or second plates and that a variable angle between the first and second plates depends on the position of the core, an inclination of at least the first plate about any axis substantially parallel to the substantially flat surfaces inducing the displacement of the core between the plates and providing freedom of movement for the patient and, at the same time, helping eliminate the positioning defects of the prosthesis.

10. The intervertebral disc prosthesis as claimed in claim 1, in which the same plates can be assembled with cores of different thicknesses.

11. The intervertebral disc prosthesis as claimed in claim 1, in which at least a part of the surface of the first plate is concave and complementary to the surface of the core with which it is in contact.

12. The intervertebral disc prosthesis as claimed in claim 1, in which the lower surface of the lower plate and the upper surface of the upper plate are provided with teeth or notches situated in the vicinity of at least two edges of the prosthesis and oriented so as to prevent sliding of the prosthesis prior to its adhesion to the osseous tissue permitted by a porous biocompatible coating of the surfaces of the plates in contact with the vertebrae.

13. The intervertebral disc prosthesis as claimed in claim 1, in which at least the second plate comprises one or more openings in the vicinity of its front side, provided to receive anchoring means of the prosthesis in a vertebra.

14. The intervertebral disc prosthesis as claimed in claim 13, in which the openings of the second plate are circular, and in that the anchoring means have the form of a stud.

15. The intervertebral disc prosthesis as claimed in any one of claim 13 or 14, in which the head of the anchoring means have larger dimensions than the openings of the second plate, the anchoring means being fixed into a vertebra, the second plate is sandwiched in between the head of the anchoring means and said vertebra.

16. The intervertebral disc prosthesis as claimed in claim 1, in which the upper plate is bulged on at least a part of its upper surface to adapt to the form of the vertebrae.

17. The intervertebral disc prosthesis as claimed in claim 1, further comprising limit stops comprising male structure and female structure allowing to limit or prevent the movements in translation of the core relative to the second plate, along an axis substantially parallel to the substantially flat surfaces, and allowing to limit or prevent the movements in rotation of the core relative to the second plate, about an axis substantially perpendicular to the substantially flat surfaces.

18. The intervertebral disc prosthesis as claimed in claim 17, in which the limit stops comprise male structure of the second plate, cooperating with female structure of the core.

19. The intervertebral disc prosthesis as claimed in claim 17, in which the dimensions of the male structure are slightly less than those of the female structure so as to permit slight clearance between the core and the second plate.

20. The intervertebral disc prosthesis as claimed in claim 17, in which the dimensions of the male structure are substantially the same as those of the female structure so as to prevent any clearance between the core and the second plate.

21. The intervertebral disc prosthesis as claimed in claim 17, in which the male structure comprises two contact plates situated on the second plate opposite one another on two edges of the prosthesis, and the female structure of the core comprises two recesses.

22. The intervertebral disc prosthesis as claimed in claim 17, in which the male structure comprises two walls situated on the second plate opposite one another in the vicinity of two edges of the prosthesis, and the female structure comprises recesses of the core.

23. The intervertebral disc prosthesis as claimed in claim 17, in which the male structure comprises two nibs of the second plate curved towards the interior of the prosthesis and situated opposite one another on two edges of the prosthesis, and the female structure comprises two recesses.

24. The intervertebral disc prosthesis as claimed in claim 23, in which at least one of the nibs is replaced by a pin equipped with a hole and on which a plate is fixed by a dowel penetrating the hole.

25. An intervertebral disc prosthesis for insertion between adjacent vertebrae, comprising:
a first plate having a curved articulation surface and a vertebral contact surface;
a second plate having a substantially flat articulation surface and a vertebral contact surface;
a core having a curved surface in contact with at least a part of the curved articulation surface of the first plate and a substantially flat surface in contact with at least a part of the substantially flat articulation surface of the second plate, the core displaceable in translation along an axis substantially parallel to the substantially flat articulation surface of the second plate and in rotation about an axis substantially perpendicular to the substantially flat articulation surface of the second plate;
plural limit stops each configured to limit translation and rotation of the core, each limit stop comprising a contact plate disposed proximal to an edge of the second plate and a cooperating recess disposed on an edge of the core, with each cooperating recess sized for clearance of the respective contact plate sufficient to provide a nonzero range of translation and rotation of the core; and
vertebral anchors disposed near edges of the vertebral contact surfaces of the first and second plates.

26. An intervertebral disc prosthesis according to claim 25 in which the intervertebral disc prosthesis has an insertion direction, and the vertebral anchors have teeth oriented to oppose displacement of the prosthesis opposite the insertion direction.

27. An intervertebral disc prosthesis according to claim 25 in which a biocompatible coating is disposed on the vertebral contact surfaces of the first and second plates.

28. An intervertebral disc prosthesis according to claim 25 in which the vertebral contact surface of the first plate is at least partially bulged, and the vertebral contact surface of the second plate is substantially flat.

29. An intervertebral disc prosthesis according to claim 25 in which the substantially flat surface of the core has a channel.

30. An intervertebral disc prosthesis according to claim 29 in which the channel is a groove.

31. An intervertebral disc prosthesis according to claim 25 configured for assembly with cores of different thicknesses.

32. An intervertebral disc prosthesis according to claim 25 in which the dimensions of the contact plate are substantially the same as the dimensions of the cooperating recess of the core to prevent relative movement between the core and the second plate.

33. An intervertebral disc prosthesis according to claim 25 in which the vertebral contact surface of the second plate forms an angle with its substantially flat articulation surface.

34. An intervertebral disc prosthesis according to claim 25 in which the first plate is angled in the postero-anterior direction.

35. An intervertebral disc prosthesis according to claim 25 in which the core is angled in the postero-anterior direction.

36. An intervertebral disc prosthesis according to claim 25 in which the limit stops are positioned near the center of the prosthesis.

37. An intervertebral disc prosthesis according to claim 25 in which the limit stops are positioned to offset the core relative to a center of the prosthesis.

38. An intervertebral disc prosthesis according to claim 37 in which the offset of the core is configured to correct a lordosis condition.

39. An intervertebral disc prosthesis for insertion between adjacent vertebrae, comprising:
a first plate having a curved articulation surface and a vertebral contact surface;
a second plate having a substantially flat articulation surface and a vertebral contact surface;
a core having a curved surface in contact with at least a part of the curved articulation surface of the first plate and a substantially flat surface in contact with at least a part of the substantially flat articulation surface of the second plate, the core displaceable in translation along an axis substantially parallel to the substantially flat articulation surface of the second plate and in rotation about an axis substantially perpendicular to the substantially flat articulation surface of the second plate;
plural limit stops each configured to limit translation and rotation of the core, each limit stop comprising a contact plate disposed proximal to an edge of the second plate and a cooperating recess disposed on an edge of the core, with each cooperating recess sized for clearance of the respective contact plate sufficient to provide a nonzero range of translation and rotation of the core; and
a porous biocompatible coating disposed on the vertebral contact surface of the first plate or the second plate or both.

40. An intervertebral disc prosthesis according to claim 39 in which the vertebral contact surface of the first plate is at least partially bulged, and the vertebral contact surface of the second plate is substantially flat.

41. An intervertebral disc prosthesis according to claim 39 in which the substantially flat surface of the core has a channel.

42. An intervertebral disc prosthesis according to claim 41 in which the channel is a groove.

43. An intervertebral disc prosthesis according to claim 39 configured for assembly with cores of different thicknesses.

44. An intervertebral disc prosthesis according to claim 39 in which the vertebral contact surface of the second plate forms an angle with its substantially flat articulation surface.

45. An intervertebral disc prosthesis according to claim 39 in which the first plate is angled in the postero-anterior direction.

46. An intervertebral disc prosthesis according to claim 39 in which the core is angled in the postero-anterior direction.

47. An intervertebral disc prosthesis according to claim 39 in which the limit stops are positioned to offset the core relative to a center of the prosthesis.

48. An intervertebral disc prosthesis according to claim 39 in which the limit stops are positioned near the center of the prosthesis.

49. An intervertebral disc prosthesis according to claim 39 in which the dimensions of the contact plate are substantially the same as the dimensions of the cooperating recess of the core to prevent relative movement between the core and the second plate.

50. An intervertebral disc prosthesis for insertion between adjacent vertebrae, comprising:
a first plate having a curved articulation surface and a vertebral contact surface;
a second plate having a substantially flat articulation surface and a vertebral contact surface;
a core having a curved surface in contact with at least a part of the curved articulation surface of the first plate and a substantially flat surface in contact with at least a part of the substantially flat articulation surface of the second plate, the core displaceable in translation along an axis substantially parallel to the substantially flat articulation surface of the second plate and in rotation about an axis substantially perpendicular to the substantially flat articulation surface of the second plate; and
a pair of limit stops, each disposed on an opposite side of the prosthesis and each comprising
a vertically oriented contact plate disposed proximal to an edge of the second plate and having first and second generally parallel planar stop surfaces, and
a recess disposed on an edge of the core and configured to cooperate with the vertically oriented contact plate, having first and second generally parallel planar stop surfaces configured to engage, respectively, the first and second planar stop surfaces of the contact plate to limit translation of the core along the substantially flat articulation surface of the second plate, with the first generally parallel planar stop surface of the recess contacting the first generally parallel planar stop surface of the vertically oriented contact plate at a first limit of translation of the core and the second generally parallel planar stop surface of the recess contacting the second generally parallel planar stop surface of the vertically oriented contact plate at a second limit of translation of the core, with the first and second limits of translation defining a nonzero range of translation and rotation of the core with respect to the second plate.

* * * * *